US007541038B2

United States Patent
Kovacs et al.

(10) Patent No.: US 7,541,038 B2
(45) Date of Patent: Jun. 2, 2009

(54) FUSOGENIC, SELF-PROPAGATING BLEBS AS IMMUNOGENIC COMPOSITIONS

(75) Inventors: Gerald Raul Kovacs, Potomac, MD (US); Xiaoyan Mo, Boxborough, MA (US); Nikolaos Vasilakis, Galveston, TX (US); Sangeeta Bhargava, Potomac, MD (US); Timothy Joseph Zamb, Nyack, NY (US); Stephen Alexander Udem, New York, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/559,429

(22) PCT Filed: Jun. 2, 2004

(86) PCT No.: PCT/US2004/017127

§ 371 (c)(1),
(2), (4) Date: Nov. 20, 2006

(87) PCT Pub. No.: WO2005/016961

PCT Pub. Date: Feb. 24, 2005

(65) Prior Publication Data

US 2007/0128222 A1    Jun. 7, 2007

Related U.S. Application Data

(60) Provisional application No. 60/476,137, filed on Jun. 5, 2003.

(51) Int. Cl.
*A61K 39/155* (2006.01)
*C12N 15/86* (2006.01)

(52) U.S. Cl. .............. 424/199.1; 424/211.1; 435/320.1; 435/235.1

(58) Field of Classification Search .................. None
See application file for complete search history.

(56) References Cited

U.S. PATENT DOCUMENTS

| | | | |
|---|---|---|---|
| 4,650,764 A | 3/1987 | Temin et al. | |
| 5,091,309 A | 2/1992 | Schlesinger et al. | |
| 5,185,440 A | 2/1993 | Davis et al. | |
| 5,217,879 A | 6/1993 | Huang et al. | |
| 5,505,947 A | 4/1996 | Johnston et al. | |
| 5,512,421 A | 4/1996 | Burns et al. | |
| 5,580,564 A | 12/1996 | Glazenburg et al. | |
| 5,643,576 A | 7/1997 | Johnston et al. | |
| 5,670,354 A | 9/1997 | Burns et al. | |
| 5,792,462 A | 8/1998 | Johnston et al. | |
| 6,156,558 A | 12/2000 | Johnston et al. | |
| 6,475,780 B1 * | 11/2002 | Parrington et al. | ....... 435/320.1 |
| 6,497,873 B1 | 12/2002 | Whitt et al. | |
| 6,531,135 B1 | 3/2003 | Johnston et al. | |
| 2003/0148262 A1 * | 8/2003 | Polo et al. | ....................... 435/5 |
| 2004/0208848 A1 * | 10/2004 | Smith et al. | ................ 424/93.2 |

FOREIGN PATENT DOCUMENTS

| | | |
|---|---|---|
| WO | WO 01/55330 A2 | 8/2001 |
| WO | WO 01/92548 A2 | 12/2001 |
| WO | WO 02/080983 A1 | 10/2002 |
| WO | WO 02/089728 A2 | 11/2002 |
| WO | WO 02/095023 A2 | 11/2002 |

OTHER PUBLICATIONS

Villar et al (Glycoconjugate Journal 23:5-17, 2006, not prior art).*
Chen et al, Journal of Immunology 169:3208-3216, 2002.*
Henrickson (Clinical Microbiology Reviews 16:242-264, 2003).*
Chin, J.; et al.; American Journal of Epidemiology 89(4):449-463 (1969).
Counihan, M.E.; et al.; Pediatr Infect Dis J 20:646-653 (2001).
Crowe, J.E. Jr.; et al.; Virus Genes 13(3):269-273 (1996).
Davis, N.L.; et al.; Journal of Virology 70(6):3781-3787 (Jun. 1996).
Durbin, A.P.; et al.; Virology 234:74-83 (1997).
Durbin, A.P., et al.; Virology 235;323-332 (1997).
Durbin, A.P.; et al.; Vaccine 16(13):1324-1330 (1998).
Ebata, S.N.; et al.; Virology 183:437-441 (1991).
Elango, N.; et al.; Proc. Natl. Acad. Sci. 83:1906-1910 (1986) Abstract Only.
Haller, A.A.; et al.; J. Virology 74(24):11626-11635 (2000).
Jones, T.; Current Opinion in Investigational Drugs 2(7):890-892 (2001).
Kahn, S.J.; et al.; J. Virology 75(22):11079-11087 (2001).
Kim, H.W.; et al.; American Journal of Epidemiology 89(4):422-434 (1969).
Lee, J.S.; et al.; J. Infect. Dis. 185(8):1192-1196 (2002).
MacDonald, G.H.; et al.; Journal of Virology 74(2):914-922 (2000).
Ojkic, D.; et al.; Intervirology 40:253-262 (1997).
Paredes, A.; et al.; Journal of Virology 75(19):9532-9537 (Oct. 2001).
Pedersen, C.E. Jr. and Eddy, G.A.; Journal of Virology 14(4):740-744 (1974).
Peroulis, I.; et al.; Arch Virol 144:107-116 (1999).
Pushko, et al.; Virology 239:389-401 (1997).
Stokes, A.; et al.; Virus Research 25:91-103 (1992).
Strauss, J.H and Strauss, E.G.; Microbiological Reviews 58(3):491-562 (1994).

* cited by examiner

*Primary Examiner*—Mary E Mosher
(74) *Attorney, Agent, or Firm*—J. Darrell Fontenot

(57) ABSTRACT

Self-propagating, fusogenic blebs are produced from cells infected with a population of Venezuelan Equine Encephalitis virus replicon particles (VRP). The self-propagating, fusogenic nature of the blebs is derived from expression of heterologous genes encoding viral fusion proteins that are incorporated into the replication defective replicon particles. The resulting blebs can be harvested from supernatants of cells displaying severe cytopathic effects. The blebs are used to make immunogenic compositions and devise methods of immunizing mammals against paramyxoviruses such as parainfluenza virus type 3.

62 Claims, 1 Drawing Sheet

FUSOGENIC, SELF-PROPAGATING BLEBS AS IMMUNOGENIC COMPOSITIONS

FIELD OF THE INVENTION

Figure 1:
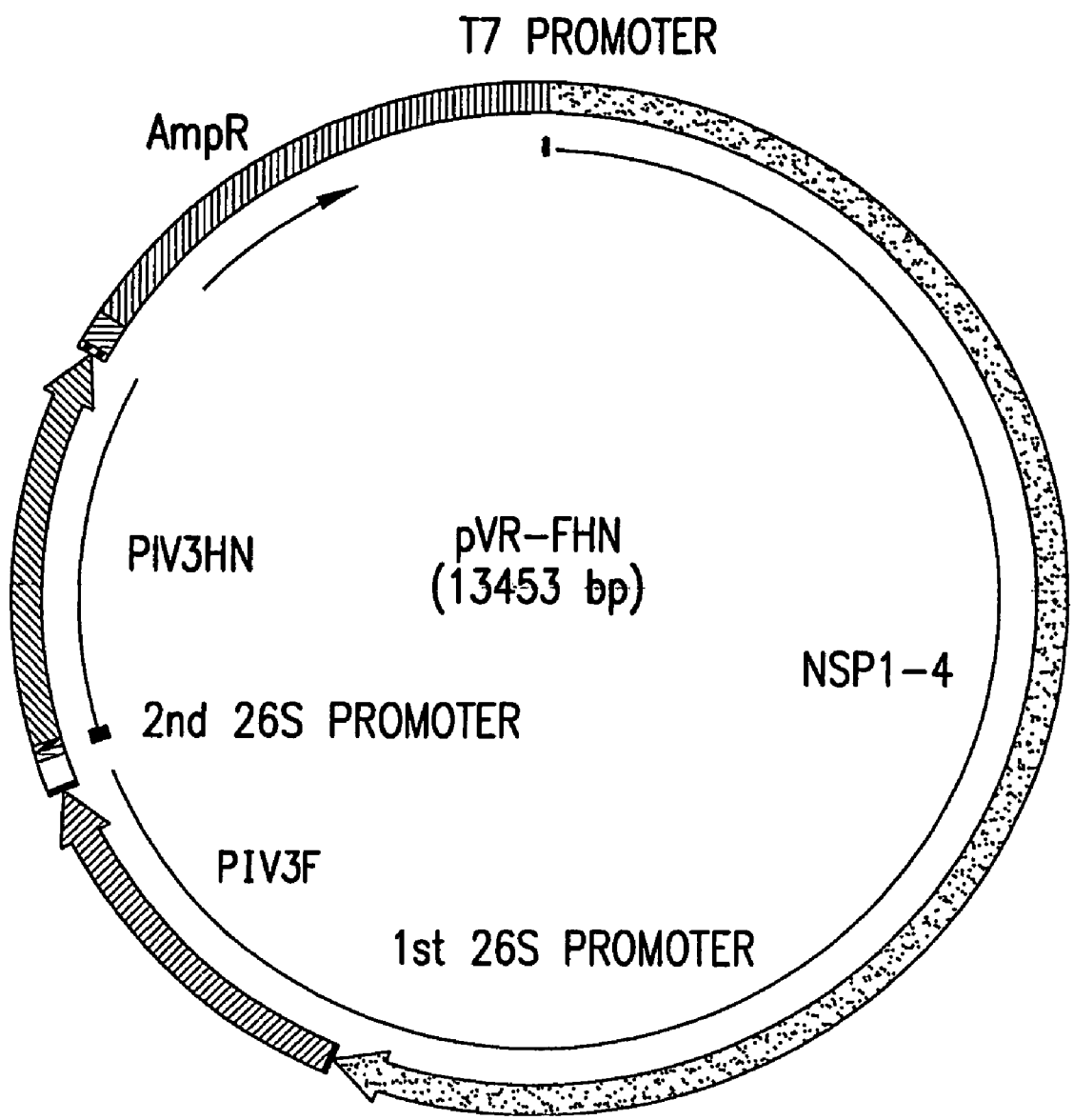

This invention relates to the field of immunogenic compositions for treating or preventing infectious diseases caused by paramyxoviruses such as parainfluenza virus type 3. This invention also relates to the field of recombinant DNA and methods of expressing foreign genes in host cells.

BACKGROUND OF THE INVENTION

The paramyoviruses are enveloped, negative-sense, non-segmented single stranded RNA viruses whose members can be extremely infectious, prevalent and disease causing. Examples include measles, mumps, respiratory syncytial virus and the parainfluenza viruses. Concerted efforts are being organized by the World Health Organization (WHO) to try to eradicate paramyxoviruses such as the measles virus. Other paramyxoviruses, such as the Newcastle disease, virus wreak havoc on farm animal populations.

In the United States, respiratory syncytial virus (RSV) and parainfluenza virus (PIV) types 1, 2 3, and 4, are the major cause of hospitalization for respiratory illness in young children as well as in adults. For example, RSV and PIV together account for the majority of cases of bronchiolitis and croup in children. Likewise, RSV and PIV, account for nearly half of the cases of pneumonia and flu-like illness in children. In addition, both viruses can be transmitted via aerosol droplets and thus contribute to nosocomial infections.

Attempts to alleviate the impact of RSV and PIV on human health and on the world economy has been ongoing for more than 30 years with little success. For example, vaccine development in RSV was hampered early on by disappointing results with a formalin inactivated whole virus RSV vaccine. In this incident, subjects immunized with formalin inactivated whole virus contracted more severe disease following immunization. See Kim et al, *Am. J. Epidemiol.* 89:422-434 (1969). Previous attempts to make efficacious formaldehyde-inactivated PIV and RSV vaccine had failed to provide appropriate protection against infection. See Chin, J., et al., *Am. J. Epidemiol.* 89:449-463 (1969).

Currently two live attenuated vaccine candidates, a cold-passage derivative (cp45) of PIV3 (JS strain) and a bovine parainfluenza virus type 3 have been evaluated in clinical trials. See Jones, T., *Current Opinion in Investigational Drugs,* 2(7):890-892 (2001). As a result, cp45 is considered a promising PIV3 vaccine.

Another important aspect of RSV and PIV research remains prevention of disease complications in elderly people or in those with existing medical conditions such as pneumonia and lower respiratory tract infections. In this regard, there have been attempts to develop vector-based and purified protein antigens for administration to affected patient populations. See Crowe, J. E., et al. *Virus Genes* 13(3): 26-273 (1996).

A variety of vectors have been examined for their ability to incorporate and express heterologous genes of paramyxoviridae family viruses. These include, for example, wild type vaccinia or an attenuated Modified Ankara vaccinia (MVA) (Durbin et al., *Vaccine* 16:1234-1330 (1998); Elango, N., et al. *Proc. Natl. Acad. Sci. USA* 83:1906-1910 (1986)) replication-competent human adenovirus vector (Mittal S. K., et al., *Intervirology* 41(6):253-260 (1998)), Vesicular Stomatitis virus (VSV) (Kahn S. J., J. Virol 75(22):11079-87 (2001)), Semliki Forest virus (SFV) ((Peroulis, I., et al., *Archives of Virology,* 144:107-116 (1999), human PIV3 itself as a potential vector carrying PIV1/2 or measles virus genome (Skiadopoulos M. H., et al. *Virology* 29(1): 136-152 (2002)) and bovine PIV3 carrying human PIV3 genome (Haller A. A., et al. *J. Virology* 74(24):11626-35 (2000)). Preclinical studies with all the above vectors have showed promising protection efficacy against the corresponding pathogens.

In spite of the prevalence and severity of RSV and PIV disease and the numerous previous attempts to produce a vaccine, no immunogenic composition presently exists to prevent these infections. Therefore, a need exists for immunogenic compositions and methods of inducing protective immunity to RSV, PIV and other paramyxoviruses.

SUMMARY OF THE INVENTION

The present invention relates to immunogenic compositions for immunizing mammals against paramyxoviruses such as RSV and PIV. More particularly, the present invention relates to immunogenic compositions comprising a population of Venezuelan Equine Encephalitis virus replicon particles (VRP) comprising Venezuelan Equine Encephalitis virus replicase genes, Venezuelan Equine Encephalitis virus replicase proteins, Venezuelan Equine Encephalitis virus E1 glycoprotein, Venezuelan Equine Encephalitis virus E2 glycoprotein, parainfluenza virus type 3 F glycoprotein gene, and parainfluenza virus type 3 HN glycoprotein gene. In certain embodiments, the Venezuelan Equine Encephalitis virus replicon particles induce cytopathic effects when used to infect monolayers of BHK cultured cells. In another embodiment, supernatants from cells infected with the replicon particles, when transferred to uninfected cell monolayers induce cytopathic effects in the absence of the replicon particles. In particular embodiments, the cytopathic effect in BHK cultured cells is syncytia formation, monolayer disruption or apoptosis. In still another embodiment, the population of Venezuelan Equine Encephalitis virus replicon particles (VRP) contains no detectable replication competent Venezuelan Equine Encephalitis virus. In one embodiment, the Venezuelan Equine Encephalitis virus replicon particles elicit a protective immune response in a mammalian host. In a certain embodiment, the protective immune response prevents infection of the lower respiratory tract by parainfluenza virus type 3 in a mammalian host. In another embodiment, the protective immune response reduces the severity of infection of the upper respiratory tract by parainfluenza virus type 3 in a mammalian host. In a particular embodiment, the immunogenic composition further comprises a pharmaceutically acceptable carrier and/or an adjuvant.

In one embodiment, the present invention provides an immunogenic composition comprising a population of Venezuelan Equine Encephalitis virus replicon particles (VRP) comprising Venezuelan Equine Encephalitis virus replicase genes, Venezuelan Equine Encephalitis virus replicase proteins, Venezuelan Equine Encephalitis virus E1 glycoprotein, Venezuelan Equine Encephalitis virus E2 glycoprotein, and at least one paramyxovirus glycoprotein gene. In a certain embodiment, the paramyxovirus is selected from the group consisting of parainfluenza virus type 1, parainfluenza virus type 2, parainfluenza virus type 3, parainfluenza virus type 4 and respiratory syncytial virus. In another embodiment, the paramyxovirus glycoprotein is selected from the group consisting of parainfluenza virus type 1 HN, parainfluenza virus type 1 F, parainfluenza virus type 2 HN, parainfluenza virus type 2 F, parainfluenza virus type 3 HN, parainfluenza virus type 3 F, parainfluenza virus type 4 HN, parainfluenza virus type 4 F. In still another embodiment, both the HN and F glycoproteins for a particular parainfluenza virus are combined and are selected from the group consisting of parainfluenza virus type 1 F glycoprotein gene and parainfluenza virus type 1 HN glycoprotein gene; parainfluenza virus type 2 F glycoprotein gene and parainfluenza virus type 2 HN glycoprotein gene; parainfluenza virus type 3 F glycoprotein gene and parainfluenza virus type 3 HN glycoprotein gene; and parainfluenza virus type 4 F glycoprotein gene and parainfluenza virus type 4 HN glycoprotein gene. In an alternate embodiment, the paramyxovirus is respiratory syncytial virus and the glycoprotein is respiratory syncytial virus attachment (G) glycoprotein, and/or respiratory syncytial virus Fusion (F) glycoprotein. In one embodiment of the present invention the Venezuelan Equine Encephalitis virus replicon particles induce cytopathic effects when used to infect monolayers of BHK cultured cells. In another embodiment, supernatants from cells infected with the replicon particles, when transferred to uninfected cell monolayers induce the cytopathic effects in the absence of the replicon particles. In a particular embodiment of the present invention, the cytopathic effect is selected from the group consisting of syncytia formation, monolayer disruption and apoptosis.

In one embodiment, the present invention provides an isolated recombinant nucleic acid molecule encoding a Venezuelan Equine Encephalitis virus replicase, a parainfluenza virus type 3 F glycoprotein, and a parainfluenza virus type 3 HN glycoprotein. In another embodiment, the present invention provides an isolated recombinant nucleic acid molecule encoding a Venezuelan Equine Encephalitis virus replicase, a parainfluenza virus type 3 F glycoprotein, and a parainfluenza virus type 3 HN glycoprotein having the nucleic acid sequence shown in SEQ ID NO: 4. In an alternate embodiment, the Venezuelan Equine Encephalitis virus replicase, the parainfluenza virus type 3 F glycoprotein, and the parainfluenza virus type 3 HN glycoprotein are encoded by the nucleic acid shown in SEQ ID NO: 1. In a particular embodiment, the Venezuelan Equine Encephalitis virus replicase, the parainfluenza virus type 3 F glycoprotein, and the parainfluenza virus type 3 HN glycoprotein comprise the amino acid sequences set forth in SEQ ID NO:2; SEQ ID NO:3, and SEQ ID NO:4. In another embodiment, the immunogenic composition further comprises a pharmaceutically acceptable carrier and/or an adjuvant.

In one embodiment, the present invention provides a method of immunizing a mammalian subject against infection of the respiratory tract by a paramyxovirus, which method comprises administering to the subject an immunologically effective amount of: (a) an immunogenic composition comprising a population of Venezuelan Equine Encephalitis virus replicon particles (VRP) comprising Venezuelan Equine Encephalitis virus replicase genes, Venezuelan Equine Encephalitis virus replicase proteins, Venezuelan Equine Encephalitis virus E1 glycoprotein, Venezuelan Equine Encephalitis virus E2 glycoprotein and at least one paramyxovirus glycoprotein gene; and (b) a pharmaceutical acceptable carrier, in an amount sufficient to elicit the immune response. In a specific embodiment, the paramyxovirus is parainfluenza virus type 3, and the glycoprotein is parainfluenza virus type 3 Hemagglutinin-Neuraminidase (HN) glycoprotein or parainfluenza virus type 3 Fusion (F) glycoprotein. In another embodiment, glycoprotein includes both parainfluenza virus type 3 F glycoprotein and HN glycoproteins. In still another embodiment, supernatants from cells infected with the replicon particles, when transferred to uninfected cell monolayers induce cytopathic effects in the absence of the replicon particles. In particular embodiments, the cytopathic effect in BHK cultured cells is syncytia formation, monolayer disruption or apoptosis. In a particular embodiment, the population of Venezuelan Equine Encephalitis virus replicon particles (VRP) contains no detectable replication competent Venezuelan Equine Encephalitis virus. In another embodiment, the paramyxovirus is paramyxovirus is respiratory syncytial virus and the glycoprotein is respiratory syncytial virus attachment (G) glycoprotein or the respiratory syncytial virus Fusion (F) glycoprotein. In an alternate embodiment, the glycoprotein includes both respiratory syncytial virus G glycoprotein and F glycoprotein. In a certain embodiment, the infection is in the lower respiratory tract. While in another embodiment, the infection is in the upper respiratory tract.

The present invention also provides immunogenic compositions comprising a population of self-propagating blebs comprising the Venezuelan Equine Encephalitis virus replicase genes, Venezuelan Equine Encephalitis virus replicase proteins, parainfluenza virus type 3 F glycoprotein gene, parainfluenza virus type 3 F glycoprotein, parainfluenza virus type 3 HN glycoprotein gene and parainfluenza virus type 3 HN glycoprotein. In a particular embodiment, the blebs are fusogenic. In another embodiment, the self-propagating blebs are obtained from the supernatant of cells infected with a population of Venezuelan Equine Encephalitis virus replicon particles (VRP), the replicon particles comprising the Venezuelan Equine Encephalitis virus replicase genes, Venezuelan Equine Encephalitis virus replicase proteins, Venezuelan Equine Encephalitis virus E1 glycoprotein, Venezuelan Equine Encephalitis virus E2 glycoprotein, a parainfluenza virus F glycoprotein gene, and a parainfluenza virus HN glycoprotein gene. In another embodiment, the self-propagating blebs induce cytopathic effects when used to infect monolayers of BHK cultured cells. More particularly, supernatants from cells infected with the self-propagating blebs, when transferred to uninfected cell monolayers induce cytopathic effects in the absence of the replicon particles. In a particular embodiment of the present invention, the blebs induce one or more of the following cytopathic effects in BHK cultured cells: syncytia formation, monolayer disruption and apoptosis. In another embodiment, the bleb population contains no detectable replication competent Venezuelan Equine Encephalitis virus. In a certain embodiment, the self-propagating blebs elicit a protective immune response in a mammalian host. In a particular embodiment, the protective immune response prevents infection of the lower respiratory tract by parainfluenza virus type 3 in a mammalian host. In another embodiment, the protective immune response prevents infection or reduces the severity of infection in the upper respiratory tract by parainfluenza virus type 3 in a mammalian host.

Embodiments of the present invention provide methods of immunizing a mammalian subject against infection by a paramyxovirus. For example, one such method comprises administering to a subject an immunologically effective amount of an immunogenic composition comprising a population of self-propagating blebs comprising (a) Venezuelan Equine Encephalitis virus replicase genes, Venezuelan Equine Encephalitis virus replicase proteins, at least one paramyxovirus glycoprotein gene and at least one paramyxovirus glycoprotein, (b) a pharmaceutical acceptable carrier, and the immunogenic composition is administered in an amount sufficient to elicit the immune response. In a certain embodiment, the self-propagating blebs are obtained from the supernatant of cells infected with a population of Venezuelan Equine Encephalitis virus replicon particles (VRP), the replicon particles comprising the Venezuelan Encephalitis virus replicase genes, Venezuelan Equine Encephalitis virus replicase proteins, Venezuelan Equine Encephalitis virus E1 glycoprotein, Venezuelan Equine Encephalitis virus E2 glycoprotein, and at least one paramyxovirus glycoprotein gene. In certain embodiments, the paramyxovirus is selected from the group consisting of parainfluenza virus type 1, parainfluenza virus type 2, parainfluenza virus type 3, parainfluenza virus type 4 and respiratory syncytial virus. In another embodiment, the paramyxovirus glycoprotein is selected from the group consisting of parainfluenza virus type 1 HN, parainfluenza virus type I F, parainfluenza virus type 2 HN, parainfluenza virus type 2 F, parainfluenza virus type 3 HN, parainfluenza virus type 3 F, parainfluenza virus type 4 HN, parainfluenza virus type 4 F. In a specific embodiment, both the HN and F glycoproteins for a particular parainfluenza virus are combined and are selected from the group consisting of parainfluenza virus type 1 F glycoprotein gene and parainfluenza virus type 1 HN glycoprotein gene; parainfluenza virus type 2 F glycoprotein gene and parainfluenza virus type 2 HN glycoprotein gene; parainfluenza virus type 3 F glycoprotein gene and parainfluenza virus type 3 HN glycoprotein gene; and parainfluenza virus type 4 F glycoprotein gene and parainfluenza virus type 4 HN glycoprotein gene. In another embodiment, the paramyxovirus is respiratory syncytial virus and the glycoprotein is respiratory syncytial virus attachment (G) glycoprotein, and/or respiratory syncytial virus Fusion (F) glycoprotein. In another embodiment, the blebs are fusogenic. In one embodiment of the present invention the blebs induce cytopathic effects when used to infect monolayers of BHK cultured cells. In another embodiment, supernatants from cells infected with the blebs, when transferred to uninfected cell monolayers induce the cytopathic effects in the absence of the replicon particles. In a particular embodiment of the present invention, the cytopathic effect is selected from the group consisting of syncytia formation, monolayer disruption and apoptosis.

In an alternate embodiment, the immunogenic composition comprising self-propagating fusogenic blebs further comprises a pharmaceutically acceptable carrier. In another embodiment, the immunogenic composition comprising self-propagating fusogenic blebs further comprises an adjuvant.

The present invention also provides a method of immunizing a mammalian subject against infection of the respiratory tract by a paramyxovirus, which method comprises administering to said subject an immunologically effective amount of: (a) an immunogenic composition comprising a population of self-propagating blebs comprising Venezuelan Equine Encephalitis virus replicase genes, Venezuelan Equine Encephalitis virus replicase proteins, a parainfluenza virus F glycoprotein gene, a parainfluenza virus F glycoprotein, a parainfluenza virus HN glycoprotein gene and a parainfluenza virus HN glycoprotein; (b) a pharmaceutical acceptable carrier, and in an amount sufficient to elicit the immune response. In one embodiment, the self-propagating blebs are obtained from the supernatant of cells infected with a population of Venezuelan Equine Encephalitis virus replicon particles (VRP), said replicon particles comprising the Venezuelan Equine Encephalitis virus replicase genes, Venezuelan Equine Encephalitis virus replicase proteins, Venezuelan Equine Encephalitis virus E1 glycoprotein, Venezuelan Equine Encephalitis virus E2 glycoprotein, a parainfluenza virus F glycoprotein gene, a parainfluenza virus HN glycoprotein gene. In a certain embodiment, the population contains no detectable replication competent Venezuelan Equine Encephalitis virus and supernatants from cells infected with the self-propagating blebs when transferred to uninfected cell monolayers induce cytopathic effects in the absence of the replicon particles. In another embodiment, the parainfluenza virus is selected from the group consisting of parainfluenza virus type 1, parainfluenza virus type 2, parainfluenza virus type 3, and parainfluenza virus type 4. In another embodiment, the HN glycoprotein is parainfluenza virus type 3 Hemagglutinin-Neuraminidase (HN) glycoprotein and the F glycoprotein is parainfluenza virus type 3 Fusion (F) glycoprotein. In a particular embodiment, the glycoprotein includes both parainfluenza virus type 3 F glycoprotein and HN glycoproteins.

In one embodiment, the present invention provides a method of immunizing a mammalian subject against infection by parainfluenza virus type 3, which method comprises administering to said subject an immunologically effective amount of: (a) an immunogenic composition comprising a population of self-propagating blebs comprising Venezuelan Equine Encephalitis virus replicase genes, Venezuelan Equine Encephalitis virus replicase proteins, parainfluenza virus type 3 F glycoprotein gene, parainfluenza virus type 3 F glycoprotein, parainfluenza virus type 3 HN glycoprotein gene, and parainfluenza virus type 3 HN glycoprotein, ; (b) a pharmaceutical acceptable carrier, and in an amount sufficient to elicit the immune response. In another embodiment, the Venezuelan Equine Encephalitis virus replicase proteins, parainfluenza virus type 3 F glycoprotein, and parainfluenza virus type 3 HN glycoprotein have the amino acid sequences shown in SEQ ID NO: 2, SEQ ID NO: 3 and SEQ ID NO: 4. In a particular embodiment, the self-propagating blebs are obtained from the supernatant of cells infected with a population of Venezuelan Equine Encephalitis virus replicon particles (VRP), said replicon particles comprising the Venezuelan Equine Encephalitis virus replicase genes, Venezuelan Equine Encephalitis virus replicase proteins, Venezuelan Equine Encephalitis virus E1 glycoprotein, Venezuelan Equine Encephalitis virus E2 glycoprotein, parainfluenza virus type 3 F glycoprotein gene, parainfluenza virus type 3 HN glycoprotein gene; in an amount sufficient to elicit the immune response. In another embodiment the population contains no detectable replication competent Venezuelan Equine Encephalitis virus. In a particular embodiment, supernatants from cells infected with the self-propagating blebs, when transferred to uninfected cell monolayers induce said cytopathic effects in the absence of the replicon particles.

BREIF DESCRIPTION OF THE DRAWINGS

FIG. 1 is a depiction of the VRP-F/HN replicon plasmid showing the VEE replicase gene, PIV3 F gene and PIV3 HN gene.

DETAILED DESCRIPTION OF THE INVENTION

Alphaviruses have been genetically engineered as mammalian and insect cell gene delivery systems for in vivo and ex vivo uses. Alphavirus genomes consist of a single, positive-sense RNA that is divided into two regions, the 5' nonstructural protein (NSP) gene followed by a subgenomic promoter that regulates the transcription of the structural genes. The NSP gene is translated immediately after the viral core is released into the cytoplasm. The NSP complex functions as a replicase to synthesize full-length antigenomes and genomes, and as a transcriptase synthesizing subgenomic transcripts encoding the structural genes Exemplary alphaviruses include the Venezuelan equine encephalitis (VEE) virus, Sindbis virus, and Semiliki Forest virus.

Replication of alphaviruses is independent of the structural genes; therefore, they can be removed and a foreign gene put in their place. Introduction of such a recombinant RNA into cells results in one round of replication and expression of the foreign gene product. As such, these genomes are termed "suicide" vectors or "replicons". The two major advantages of delivering foreign genes with alphavirus vectors are: 1) a high level of expression is obtained, and 2) apoptosis (or programmed cell death) of the infected cell, which results in "danger" signals that alert the immune system and elicit robust immune responses.

A replicon vector may be used in the form of naked RNA, incorporated as cDNA into eukaryotic pol II promoter-based plasmid delivery vehicles, or alternatively packaged into infectious virus-like replicon particles. Effective delivery of the replicon vector results in robust foreign gene expression and programmed cell death. In all instances, the vector undergoes only one round of replication and, unlike a live virus, ceases to spread from cell to cell.

The replicon system is described in detail in the following U.S. patents: U.S. Pat. No. 5,185,440 entitled "cDNA clone coding for Venezuelan equine encephalitis virus and attenuating mutations thereof" to N. L. Davis et al.; U.S. Pat. No. 5,505,947 entitled "Attenuating mutations in Venezuelan equine encephalitis virus" to R. E. Johnston et al.; U.S. Pat. No. 6,156,558 entitled "Alphavirus RNA replicon systems" to R. E. Johnston et al.; and U.S. Pat. No. 6,531,135 entitled "Alphavirus RNA replicon systems" to R. E. Johnston et al., the disclosures of which are hereby incorporated by reference in their entirety.

This present invention describes a novel method by which to deliver replicon expression vectors. A Venezuelan equine encephalitis virus (VEE) replicon vector was genetically engineered to simultaneously express the hemagglutinin (HN) and fusion (F) proteins of a paramyxovirus, parainfluenza virus type 3 (PIV3). During characterization of the VEE replicon particles (VRP), it was observed that, contrary to what is known about replicons, this system produced infectious particles upon VRP-F/HN replicon infection in tissue culture. These infectious particles: 1) expressed PIV3 HN, F, and the VEE NSP complex, 2) were capable of self-propagating, 3) contained the HN and F proteins on their surface, 4) were stable through repeated freeze-thaw cycles, 5) were heterogenous in size and part of them filterable though 0.2 micron filters, 6) were highly immunogenic and 7) could be used as an effective immunogenic composition against PIV3 infection in a Syrian Hamster model. The invention is described in detail below.

In the course of these studies, the PIV3 HN and F genes were cloned into a replicon vector. The resulting vector (VRP-F/HN) was highly immunogenic and protected hamsters from PIV3 infection at doses as low as $1\times10^4$ infectious units (IU), by intranasal or intramuscular routes. The coexpression of HN and F during VRP packaging results in large syncytia formation; consequently it was observed that the titers of this particular VRP never reached more than $1\times10^5$ VRP per packaging reaction, a titer $10^{4-5}$ lower than other VRP vectors.

Infectious or "self propagating" blebs could be produced by infecting cells with VRP-F/HN, or alternatively by transfecting cells with the VEE-F/HN replicon vector RNA alone. "Infectious blebs" or "self propagating blebs" refers to outer membrane fusogenic vesicles or fusogenic particles having PIV3 HN and F genes or some other viral fusion protein or proteins on the surface and capable of self propagation. The terms "infectious blebs", "self propagating blebs", blebs, and "fusogenic particles" will occasionally be used interchangeably. Blebs, when administered as an immunogenic composition, were able to protect the upper and lower respiratory tracts of Syrian hamsters against PIV3 infection at doses as low as $10^4$ syncytium forming units (SFU). These preclinical studies demonstrated that infectious particles could be used as immunogenic compositions for PIV3.

The present invention has several immediate utilities. First, the use of VEE replicon particles to simultaneously express the HN and F genes of PIV3. Second, the use of VEE replicon particles to generate self propagating blebs having PIV or other fusogenic proteins/glycoproteins on the surface. Third, the use of fusogenic self-propagating blebs as immunogens.

In one embodiment of the present invention, co-expression of the HN and F genes was shown to be more effective than expression of either gene alone, or in combination [HN+F] after individual expression, at generating immunity against PIV3 in a Syrian Hamster model. Without being bound by theory, the immunogenicity of this vector may be related to an enhanced level of presentation and/or longer half-life of the F/HN complex. Alternatively, fusogenic particles or blebs released from the infected cells may enhance the longevity of expression and/or the number of cells that become infected.

In another embodiment of the present invention, fusogenic particles or blebs containing the HN and F proteins on their surface were also effective immunogenic compositions against PIV3 infection in the Syrian hamster model. Approximately, 10-100 blebs are produced per infected cell in vitro, making this system suitable for large-scale production. Blebs were stable through freeze-thaw cycles. Self-propagating blebs may be generated by infecting cells with VRP-F/HN or with blebs, or alternatively by electroporation of VEE replicon-F/HN RNA.

One particular embodiment of the present invention is to include an additional one or two genes that could confer protection against a heterologous pathogen. The fact that fusogenic particles are self-propagating offers an advantage over in-vitro generated immunogenic compositions. For example, other fusogenic proteins from other viruses (measles, SV5, or HIV) may also be utilized in place of PIV3 HN and F, thus enhancing the repertoire of the immunogenic compositions.

Replicons derived from Venezuelan equine encephalitis virus (VEEV) represent an alternative vector system for the design of immunogenic compositions. VEE replicons have been shown capable of infecting a variety of animal cell types. VEE replicons have been used for antigen delivery of viral as well as bacterial antigens [Davis N. L., et al., *J. Virology* 70(6):3781-3787 (1996); Lee J. S., et al., *J. Infect Dis.*, 185 (8):1192-6 (2002)], and successfully induce strong humoral as well as cell mediated immunity by targeting to dendritic cells [MacDonald G. H., et al. *J. Virology*, 74(2):914-922 (2000)].

VEE replicons exploit certain properties of the parent Venezuelan equine encephalitis virus. Venezuelan equine encephalitis virus (VEE) is a member of the alphavirus genus of the Togaviridae. The viral genome is a single-stranded, positive-sense RNA, modified at the 5'-end with a methylated cap, and at the 3'-end with a variable-length poly (A) tract. Structural subunits containing a single viral capsid protein (c) associate with the RNA genome in an icosahedral nucleocapsid. In the virion, the capsid is surrounded by a lipid envelope covered with a regular array of transmembranal protein spikes, each of which consists of a heterodimeric complex of two glycoproteins, E1 and E2. See Pedersen, C. E. and Eddy, G. A., *J. Mol. Biol.* 168:1-15 (1974). The organization of the VEE genome and the overall strategy of VEE gene expression parallels those of the prototype alphaviruses, Sindbis virus and Semliki Forest virus. (For a review see Schlesinger, S. and Schlesinger, M. J., *The Togaviridae and*

*Flaviviridae*. Plenum Publishing Corp., New York (1986). For example, details of the partial genome sequence of the Trinidad Donkey strain of VEE reveal that VEE structural proteins are translated in the form of a polyprotein from a 26S subgenomic mRNA which corresponds to the 3' one-third of the viral genome. See Kinney et al., Virology 152:400 (1986). Proteolytic processing produces the proteins found in the mature virion. Alphavirus nonstructural protein genes are located in the 5' two-thirds of the genome in the order NSP1, NSP2, NSP3 and NSP4. The proteins are expressed initially as polyprotein precursors and then proteolytically processed to their mature forms. The mature nonstructural proteins are required for replication of genome RNA and synthesis of 26S subgenomic mRNA.

The VEE genome consists of a positive sense single stranded RNA molecule. It is about 11 kb in length with a 5'-cap structure and a 3'-poly A tail. Replication proceeds through a minus-strand RNA intermediate, which is used as template for the synthesis of additional viral genomes and for the transcription of a subgenomic mRNA. When used as vector for gene delivery, the 3' one-third of the genome that encodes viral structural proteins which is dispensable for viral RNA replication, is deleted and replaced with gene(s) encoding antigen(s) of interest. Packaging of these replicons is achieved by cotransfecting defective helper RNAs that encode the VEE structural proteins. The resulting replicon particles incorporate gene(s) encoding antigen(s) of interest, but are no longer capable of generating infectious viral particles. However, the replicons can direct expression of large amounts of heterologous gene product, and thus serve as an effective tool to deliver antigens.

In order to evaluate whether VEE replicons can be used as vectors in the design of immunogenic compositions for the paramyxoviridae family virus, PIV3 virus was chosen due to its wide use as an experimental virus for research on immunogenic compositions for paramyxoviruses. Development of PIV and RSV subunit vaccines have been hampered by a lack of full understanding of the antigenicity and immunogenicity of individual virus proteins themselves. For example, the PIV3 genome contains six open reading frames (ORFs), which encode the following non-structural internal proteins: nucleocapsid (NP), matrix (M), phosphoprotein (P), the large polymerase (L) protein and two surface glycoproteins, hemagglutinin neuroaminidase (HN), and fusion (F). The ORFs also encode two other proteins C and V that are expressed due to RNA editing and alternate translation initiation, respectively. A third protein D is possibly expressed, but the function of this protein is undetermined at the present time. So far, very little information is available about the role of these internal proteins in protection against PIV3 infection. Nucleoprotein (NP) of PIV1, which shares about 85% homology to the NP of PIV3, has been shown to encode a dominant MHC class I binding peptide and induced very strong MHC class I-restricted responses and could protect mice from PIV1 infection. Also, HN and F are two major neutralizing antigens that contain at least six neutralizing sites for HN and eight for F protein.

HN is a type II glycoprotein which possesses internal hemagglutation and neuroaminidase activities. HN mediates viral attachment to cells and promotes the fusion process. It removes sialic acid to release virus particles and prevent aggregation. F protein is a type I glycoprotein and is important for virus penetration and syncytium formation. Proteolytic cleavage of Fo yields two disulfide bond linked subunits, F1 and F2 and is necessary for fusion activity. The coexistence of HN and F on the viral surface seems to have important biological consequences since in vitro fusion activity of F requires the presence of the HN protein. Preclinical studies on immunogenic compositions containing PIV3 subunits have yielded data on the importance of using HN and F as preventive antigens.

In general, the design of immunogenic compositions against paramyxoviruses such as parainfluenza viruses (PIV) and respiratory syncytial virus (RSV) is directed to prevention of infection in the lower respiratory tract (LRT). For example, adjuvant-assisted purified or vector-expressed PIV3 HN proteins provide protection against LRT in animal models, while purified or vector-expressed F protein provided partial or no protection. Approaches using a combination of recombinant HN and F or the chimeric protein F/HN showed protection against LRT infection. Studies were initiated as described herein to construct VRPs that simultaneously expressed HN and F proteins. An effective VEE-based PIV subunit immunogenic composition is described herein, with a novel feature that may potentially contribute to its strong potency.

As used herein, the terms "infectious blebs", or "self-propagating blebs" or "blebs" refers to outer membrane fusogenic vesicles having PIV3 HN and F genes (or some other viral fusion protein or proteins) on the surface, which are capable of self-propagation. The terms "infectious blebs", "self propagating blebs", blebs, and "fusogenic particles" will occasionally be used interchangeably. The self-propagation is protein-driven through the fusion protein on the bleb surface. However, the blebs also contain replicon RNA, so that upon fusing with a new cell the replicon RNA is transcribed and the fusion protein or proteins are expressed on the cell surface and the process begins again. The self-propagating blebs of the present invention were shown to be effective as immunogenic compositions against PIV3. Approximately 10-100 self-propagating blebs were produced per infected cell in vitro, making this system suitable for large-scale production. Self-propagating blebs were stable through freeze-thaw cycles. Self-propagating blebs were generated by infecting cells with VRP-F/HN or with fusogenic particles, or alternatively by electroporation of VEE replicon-F/HN RNA. The fact that infectious blebs are self-propagating offers an advantage over in-vitro generated subunit proteins.

The term "alphavirus" has its conventional meaning in the art, and includes the various species of alphaviruses such as Eastern Equine Encephalitis virus (EEE), Venezuelan Equine Encephalitis virus (VEE), Western Equine Encephalitis virus (WEE), Sindbis virus, South African Arbovirus No. 86, Semliki, Forest virus, and others. For a review see *Field's Virology*, 4$^{th}$ *Edition, Chapter* 30: *Alphaviruses* pp. 917-962 by Griffin, D. E., Publisher Lippincott Williams & Wilkins, New York (2001), the disclosure of which is hereby incorporated by reference in its entirety. The preferred alphavirus RNA transcripts for use in the present invention include VEE, Sindbis virus and Semliki Forest virus.

Alphavirus-permissive cells employed in the methods of the present invention are cells, which upon transfection with the viral RNA transcript, are capable of producing viral particles. Alphaviruses have a broad host range. Examples of suitable mammalian host cells include, but are not limited to Vero cells, baby hamster kidney (BHK) cells, chicken embryo fibroblast (CEF) cells and rhesus monkey kidney cells (LLC-MK2).

The VRPs were propagated in cells from the BHK-21 lineage. In this case, BHK cells were derived from a CCL-10 clone to distinguish them from other BHK clonal populations that may not share the shame phenotypic characteristics. As defined herein, the cells may be referred to as BHK21 or simply BHK cells.

The term "nonstructural proteins" or "NSP" as used herein refers to the polymerase function of the replicon. For example, in Venezuelan Equine Encephalitis virus (VEE), the polymerase function is provided by NSP1, NSP2, NSP3 and NSP4 proteins translated as a single polyprotein. The nonstructural protein genes are required as part of the replicon RNA for autonomous replication.

The phrases "structural protein" or "alphavirus structural protein" as used herein refer to the encoded proteins, which are required for replication of the RNA replicon, and include the capsid protein, E1 glycoprotein, and E2 glycoprotein. As described herein, the structural proteins of the alphavirus are encoded on one or more helper RNAs (i.e., a first helper RNA and a second helper RNA). In addition, one or more structural proteins may be encoded on the same RNA molecule as the replicon RNA, provided that the region encoding at least one structural protein is deleted from the replicon RNA, such that the replicon and resulting alphavirus particle are replication-defective. As used herein, the terms "deleted" or "deletion" mean either total deletion of the specified nucleic acid segment or the deletion of a sufficient portion of the specified segment to render the segment inoperative or nonfunctional, in accordance with standard usage. See, e.g., U.S. Pat. No. 4,650,764 to Temin et al. The term "replication-defective" as used herein, means that the replicon RNA cannot form new viral particles in the host cell in the absence of the helper RNA. The replicon RNA is replication-defective inasmuch as the replicon RNA does not encode all of the alphavirus structural proteins required for replication, at least one of the required structural proteins being deleted therefrom.

The helper cell for expressing the infectious, replication-defective alphavirus particle comprises a set of RNAs, as described above. The set of RNAs include a first helper RNA and a second helper RNA. The first helper RNA includes RNA encoding at least one alphavirus structural protein but does not encode all alphavirus structural proteins. In other words, the first helper RNA does not encode at least one alphavirus structural protein; the at least one non-coded alphavirus structural protein being deleted from the first helper RNA. In one embodiment, the first helper RNA includes RNA encoding the alphavirus E1 glycoprotein, with the alphavirus capsid protein and the alphavirus E2 glycoprotein being deleted from the first helper RNA. In another embodiment, the first helper RNA includes RNA encoding the alphavirus E2 glycoprotein, with the alphavirus capsid protein and the alphavirus E1 glycoprotein being deleted from the first helper RNA. In a third embodiment, the first helper RNA includes RNA encoding the alphavirus E1 glycoprotein and the alphavirus E2 glycoprotein, with the alphavirus capsid protein being deleted from the first helper RNA.

The second helper RNA includes RNA encoding at least one alphavirus structural protein which is different from the at least one structural protein encoded by the first helper RNA. Thus, the second helper RNA encodes at least one alphavirus structural protein which is not encoded by the at least one structural protein encoded by the first helper RNA. The second helper RNA does not encode the at least one alphavirus structural protein which is encoded by the first helper RNA, thus the first and second helper RNAs do not encode duplicate structural proteins. The second helper RNA encodes a different structural protein than that encoded by the first helper RNA. In the embodiment wherein the first helper RNA includes RNA encoding only the alphavirus E1 glycoprotein, the second helper RNA may include RNA encoding one or both of the alphavirus capsid protein and the alphavirus E2 glycoprotein which are deleted from the first helper RNA. In the embodiment wherein, the first helper RNA includes RNA encoding only the alphavirus E2 glycoprotein, the second helper RNA may include RNA encoding one or both of the alphavirus capsid protein and the alphavirus E1 glycoprotein, which are deleted from the first helper RNA. In the embodiment wherein the first helper RNA includes RNA encoding both the alphavirus E1 glycoprotein and the alphavirus E2 glycoprotein, the second helper RNA may include RNA encoding the alphavirus capsid protein, which is deleted from the first helper RNA.

In one embodiment, the packaging segment or "encapsidation sequence" is deleted from at least the first helper RNA. In another embodiment, the packaging segment is deleted from both the first helper RNA and the second helper RNA.

In one embodiment wherein the packaging segment is deleted from both the first helper RNA and the second helper RNA, preferably the helper cell contains a replicon RNA in addition to the first helper RNA and the second helper RNA. The replicon RNA encodes the packaging segment and an inserted heterologous RNA. The inserted heterologous RNA may be RNA encoding a viral fusion protein, or proteins necessary for producing a fusion activity, or a peptide capable of mediating fusing activity. Typically, the inserted heterologous RNA encodes a protein or a peptide, which is desirously expressed by the host, alphavirus-permissive cell or fusion partner of the self-propagating blebs, and includes the promoter and regulatory segments necessary for the expression of that protein or peptide in that cell. Examples of suitable inserted heterologous RNA include viral RNA from a wide variety of viruses including, but not limited to parainfluenza type 1, parainfluenza type 2, parainfluenza type 3, parainfluenza type 4, respiratory syncytial virus, human immunodeficiency virus, vesicular stomatitis virus and influenza virus.

Examples of suitable viral RNA genes that may be used to provide the inserted heterologous RNA include, but are not limited to the HN and F genes of parainfluenza types 1 through 4, particularly HN and F of parainfluenza type 3, the influenza hemagglutinin gene, the influenza neuraminidase gene, the Lentivirus glycoprotein envelope gene, the HIV envelope gp160 gene, and the HIV matrix capsid fusion gene. In another embodiment of the present invention, the inserted heterologous RNA encodes respiratory syncytial virus Fusion (F) glycoprotein, respiratory syncytial virus attachment (G) glycoprotein or both the respiratory syncytial virus F and G proteins.

In one embodiment, the replicon RNA, the first helper RNA and the second helper RNA are provided on separate molecules such that a first molecule, i.e., the replicon RNA, includes RNA encoding the packaging segment and the inserted heterologous RNA encoding a fusion activity, a second molecule, i.e., the first helper RNA, includes RNA encoding at least one but not all of the required alphavirus structural proteins, and a third molecule, i.e., the second helper RNA, includes RNA encoding at least one but not all of the required alphavirus structural proteins. For example, in another embodiment of the present invention, the helper cell includes a set of RNAs which include (a) a replicon RNA including RNA encoding an alphavirus packaging sequence and an inserted heterologous RNA encoding a fusion activity, (b) a first helper RNA including RNA encoding the alphavirus E1 glycoprotein and the alphavirus E2 glycoprotein, and (c) a second helper RNA including RNA encoding the alphavirus capsid protein so that the alphavirus E1 glycoprotein, the alphavirus E2 glycoprotein and the capsid protein assemble together into alphavirus replicon particles in the host cell.

In an alternate embodiment, the replicon RNA and the first helper RNA are on separate molecules, and the replicon RNA and the second helper RNA are on a single molecule together, such that a first molecule, i.e., the first helper RNA, including RNA encoding at least one but not all of the required alphavirus structural proteins, and a second molecule, i.e., the replicon RNA and second helper RNA, including RNA encoding the packaging segment, the inserted heterologous DNA and the capsid protein. Thus, the capsid protein is encoded by the second helper RNA, but the second helper RNA is located on the second molecule together with the replicon RNA. For example, in one embodiment of the present invention, the helper cell includes a set of RNAs including: (a) a replicon RNA including RNA encoding an alphavirus packaging sequence, an inserted heterologous RNA, and an alphavirus capsid protein, and (b) a first helper RNA including RNA encoding the alphavirus E1 glycoprotein and the alphavirus E2 glycoprotein so that the alphavirus E1 glycoprotein, the alphavirus E2 glycoprotein and the capsid protein assemble together into alphavirus particles in the host cell.

As used herein, the term "cytopathic effect" (CPE) refers to pronounced morphologic changes induced in an individual cultured cell or cells by virus infection. Generally, CPEs are easily visible under a light microscope. CPEs include but are not limited to the following cell phenomena: syncytia formation, monolayer disruption, rounding, shrinkage, increased refractility, fusion, aggregation, loss of adherence or lysis. These phenomena may occur singly or in combination depending on the particular virus, cell type and conditions.

The immunogenic compositions of the present invention may contain an adjuvant. An adjuvant is a substance that enhances the immune response when administered together with an immunogen or antigen. A number of cytokines or lymphokines have been shown to have immune modulating activity, and thus may be used as adjuvants, including, but not limited to, the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms), the interferons-α, β and γ, granulocyte-macrophage colony stimulating factor (see, e.g., U.S. Pat. No. 5,078,996), macrophage colony stimulating factor, granulocyte colony stimulating factor, GSF, and the tumor necrosis factors α and β. Still other adjuvants useful in this invention include a chemokine, including without limitation, MCP-1, MIP-1α, MIP-1β, and RANTES. Adhesion molecules, such as a selectin, e.g., L-selectin, P-selectin and E-selectin may also be useful as adjuvants. Still other useful adjuvants include, without limitation, a mucin-like molecule, e.g., CD34, GlyCAM-1 and MadCAM-1, a member of the integrin family such as LFA-1, VLA-1, Mac-1 and p150.95, a member of the immunoglobulin superfamily such as PECAM, ICAMs, e.g., ICAM-1, ICAM-2 and ICAM-3, CD2 and LFA-3, co-stimulatory molecules such as CD40 and CD40L, growth factors including vascular growth factor, nerve growth factor, fibroblast growth factor, epidermal growth factor, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6. Still another adjuvant molecule includes Caspase (ICE). See, also International Patent Publication Nos. WO98/17799 and WO99/43839, incorporated herein by reference.

Suitable adjuvants used to enhance an immune response include, without limitation, MPL™ (3-O-deacylated monophosphoryl lipid A; Corixa, Hamilton, M T), which is described in U.S. Pat. No. 4,912,094, which is hereby incorporated by reference. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecanoylamino]ethyl 2-Deoxy-4-O-phosphono-3-O-[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form or as a stable emulsion.

Still other adjuvants include mineral oil and water emulsions, aluminum salts (alum), such as aluminum hydroxide, aluminum phosphate, etc., Amphigen, Avridine, L121/squalene, D-lactide-polylactide/glycoside, pluronic polyols, muramyl dipeptide, killed *Bordetella*, saponins, such as Stimulon™ QS-21 (Antigenics, Framingham, Mass.), described in U.S. Pat. No. 5,057,540, which is hereby incorporated by reference, and particles generated therefrom such as ISCOMS (immunostimulating complexes), *Mycobacterium tuberculosis*, bacterial lipopolysaccharides, synthetic polynucleotides such as oligonucleotides containing a CpG motif (U.S. Pat. No. 6,207,646, which is hereby incorporated by reference), a pertussis toxin (PT), or an *E. coli* heat-labile toxin (LT), particularly LT-K63, LT-R72, PT-K9/G129; see, e.g., International Patent Publication Nos. WO 93/13302 and WO 92/19265, incorporated herein by reference.

Also useful as adjuvants are cholera toxins and mutants thereof, including those described in published International Patent Application number WO 00/18434 (wherein the glutamic acid at amino acid position 29 is replaced by another amino acid (other than aspartic acid), preferably a histidine). Similar CT toxins or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids areinserted at amino acid positions 35 and 36).

EXAMPLES

The present invention is described by way of the following examples. However, the use of these or other examples anywhere in the specification is illustrative only and in no way limits the scope and meaning of the invention or any exemplified term. Likewise, the invention is not limited to any particular embodiment described herein. Indeed, many modifications and variations of the invention may be apparent to those skilled in the art upon reading this specification and can be made without departing from its spirit and scope.

Example 1

Plasmid Construction of VRP Expressing PIV Proteins

The present invention uses human PIV-3 as a model parainfluenza virus. Human PIV3 viral stock (Washington 47885/57 strain) was prepared as described previously. See Stokes, A. et al. *Virus Research* 25:91-103 (1992). Virus stock was purified by polyethyleneglycol (PEG) precipitation. RNA was extracted by Trizol-LS (Life Technologies) and used as template for reverse transcription PCR using the Titan One Tube RT-PCR system (Roche). Primers were used to amplify fragments spanning the entire open reading frames (ORF) of N, P, M, C, HN, and F, including a 5' Kozak consensus sequence. The resulting fragments were then digested with the following restriction endonucleases: ClaI and HindIII for F, EcoRI and BamHI for HN, PstI and EcoRI for NP, AccI and XbaI for P and C, and HindIII and XbaI for M. The resultant fragments were cloned into the shuttle plasmid, pKSR1. Subsequently, ApaI-ORF-NotI cassettes from the shuttle plasmids were subcloned into pVR200 downstream from and under the control of the VEEV 26S subgenomic promoter, generating the replicon expression plasmids pVR(NP), pVR(P), pVR(M), pVR(C), pVR(F) and pVR(HN)

To generate the replicon containing two PIV genes, a second ApaI-ORF(HN)-NotI Cassette was subcloned into the pVR(F) plasmid down stream of F gene, generating replicon plasmid pVR-F/HN that contained two exogenous genes. See FIG. 1. In addition, two helper plasmids capable of expressing the VEE capsid protein (pV3014delta520-7505delta8495-11229) or surface glycoproteins gp E1/E2 (pV3014delta520-7505delta7565-8386) were used for replicon packaging. See Pushko et al. *Virology* 239:389-401 (1997), the disclosure of which is hereby incorporated by reference in its entirety. The resulting plasmids were sequenced using dye terminator cycle sequencing and the 377 ABI DNA sequencer (Applied Biosystems, Foster City, Calif.).

Example 2

VRP Production

This example describes how VRPs were generated that expressed each of the antigens of PIV3 by electroporating RNA from the plasmids constructed in Example 1 into BHK21 cells. The original VEE plasmid pVR100, and two helper plasmid pHC(capsid) and pHC(gp E1/E2) were obtained from AlphaVax (Durham, N.C.). See Pushko et al. *Virology* 239:389-401 (1997), the disclosure of which is hereby incorporated by reference in its entirety. RT-PCR fragments of the PIV3 glycoprotein genes were cloned into pVR200 individually or pVR100 (HN and F together). The generated plasmids were then subjected to in vitro transcription to generate RNAs. The RNAs were subsequently electroporlated into BHK21 cells to generate VRPs that encoded either NP, M, P, C, F and/or HN genes (VRP-NP, -M, -P, -C, -HN, -F, -F/HN), respectively.

After obtaining the individual PIV genes and cloning them into suitable expression vectors, capped RNA transcripts were then prepared in vitro using NotI linearized plasmid templates and the mMessage mMACHINE T7 RNA polymerase kit (Ambion, Austin, Tex.). The reactions were carried out according to the manufacturers instructions. Replicon particle-producing cells were generated by electroporlating 50 μg of each RNA from either plasmid pVR(NP), pVR(M), pVR(P), pVR(C), pVR(HN), pVR(F), pVR(HN) plus pVR (F), or pVR-F/HN, together with 50 μg RNA from helper plasmids into BHK21 cells. See Pushko et al. *Virology* 239: 389-401 (1997), the disclosure of which is hereby incorporated by reference in its entirety. The treated BHK cells were then incubated in a T-175 flask at 37° C. with 5% $CO_2$. The media was composed of Dulbecco's Modification of Eagle's Medium (DMEM), with high glucose, 10% fetal calf serum and 1% sodium pyruvate. Next, culture supernatants were harvested 48 hours post electroporabon and clarified by centrifugation at 3,200 rpm. The VRPs were resuspended in PBS and titers were determined by infecting BHK21 cells and immunostaining using appropriate PIV3 specific antibodies.

Example 3

Virus Titers of VRPs and PIV

VEE replicons (VRPs) expressing PIV proteins and glycoproteins were titrated by immunohistochemistry methods. The VRPs were propagated in BHK-21 lineage. In this case, BHK cells were derived from a CCL-10 clone to distinguish them from other BHK clonal populations that may not share the shame phenotypic characteristics. As defined herein, the cells may be referred to as BHK21 or simply BHK cells. BHK21 monolayers were infected with serial diluted VEE replicons: VRP-NP; VRP-P; VRP-M; VRP-C; VRP-HN; VRP-F; VRP-F/HN and VRP-GFP, and incubated at 37° C. for 16-20 hours. Monolayers were then fixed with 1:1 Acetone/Methanol for 5 minutes and stained with either rabbit anti-VEE NSP1 protein which was expressed from bacteria, polyclonal Ab r835 or horse anti-PIV3 serum. Plaques were then detected by either cyTM3 conjugated goat anti-rabbit antibody (Jackson ImmunoResearch, West Grove, Pa.) or Horseradish peroxidase (HOURP) conjugated anti-horse Ab (Kirkegaard & Perry, Maryland, Md.) plus aminoethyl-carbazole (AEC) peroxidase substrate kit (Enzo Life Sciences, Farmingdale, N.Y.). The number of plaques was counted under a microscope and reported as infectious units per ml (iu/ml) for VEE replicons, or as syncycial forming units per ml (sfu/ml) for secondary infectious particles generated from VRP-F/HN replicon infection.

Titers of PIV3 Wash47885/57 virus stock or tissue homogenates were determined by a modified Hemadsorption assay (HAD) protocol as described. See Durbin et al., *Virology* 235:323-332 (1997); Durbin et al., *Vaccine* 16:1234-1330 (1998). Briefly, 10-fold serial diluted samples were tittered in 96-well plates of LLC-MK2 monolayers at 37° C. Supernatants were collected after 6-7 days in culture and subject to HA assay with 0.5% guinea pig erythrocytes. The mean $Log_{10}TCID50$ per ml sample was calculated.

Example 4

Animal Immunization and Challenge

Immunization of non-immune hamsters with VRP replicons expressing particular PIV proteined elicits protective immunity from subsequent PIV infection. Five to eight week old golden Syrian hamsters that were seronegative for PIV3 were immunized with VEE replicons: VRP-NP; VRP-P; VRP-M; VRP-C; that expressed PIV-3 proteins NP, P, M, C of PIV3 or GFP as control, either intranasally (i.n.) or intramuscularly (i.m.). The doses are shown in Table 1. Animals were boosted 3 weeks and 5 weeks after the initial immunization with the same dose (Table 1). Seven weeks later hamsters were challenged with $1 \times 10^6$ LogTCID$_{50}$ of PIV3 (Wash47885/57 virus strain). Four days after challenge, nasal turbinates and lung tissues were collected and homogenized. See Durbin et al., *Virology* 235:323-332 (1997); Durbin et al., *Vaccine* 16:1234-1330 (1998). PIV3 replication in these homogenates were analyzed by HAD assay as described in Example 3 above. All Golden Syrian hamsters and BALB/c mice were purchased from Charles River laboratory (Wilmington, Mass.) and housed according to the current NIH "Guide for the Care and Use of Laboratory Animals," and Federal and State Law and current operating procedures maintained by Wyeth Research's BioResources.

In one embodiment of the present invention the Venezuelan Equine Encephalitis virus replicon particles induce cytopathic effects when used to infect monolayers of BHK cultured cells. In another embodiment, supernatants from cells infected with the replicon particles, when transferred to uninfected cell monolayers induce the cytopathic effects in the absence of the replicon particles. In another embodiment of the present invention, the cytopathic effect is selected from the group consisting of syncytia formation, monolayer disruption and apoptosis.

TABLE 1

PIV-3 Internal Proteins had Minimal Efficacy as Vaccine Candidates

| Immunogen | Dose (iu/100 µl) | Route | Viral Titers (−LogTCID50/ml) URT | LRT |
|---|---|---|---|---|
| VRP-NP | $1 \times 10^7$ | i.m. | 6.00 ± 0.10 | 5.73 ± 0.13 |
|  |  | i.n. | 5.39 ± 0.08 | 5.28 ± 0.11 |
|  | $1 \times 10^7$ | i.m. | 5.67 ± 0.11 | 5.40 ± 0.10 |
| VRP-P |  | i.n. | 5.57 ± 0.05 | 5.00 ± 0.13 |
|  | $1 \times 10^6$ | i.m. | 5.87 ± 0.15 | 5.80 ± 0.13 |
| VRP-M |  | i.n.. | 5.72 ± 0.07 | 5.28 ± 0.08 |
|  | $1 \times 10^6$ | i.m. | 6.22 ± 0.10 | 5.67 ± 0.00 |
| VRP-C |  | i.n.. | 6.50 ± 0.04 | 5.22 ± 0.10 |
|  | $1 \times 10^7$ | i.m. | 6.13 ± 0.11 | 4.90 ± 0.12 |
| VRP-GFP |  | i.n. | 5.95 ± 0.31 | 5.00 ± 0.00 |
| Cp45 | $1 \times 10^5$ | i.n. | 0 | 0 |
| PBS | 100 µl | i.m. | 583 ± 0.07 | 5.61 ± 0.10 |

The ability of internal proteins of PIV3 to provide protection against PIV3 infection in animals was investigated using hamsters as an experimental model, because hamsters are the smallest animal model that support PIV3 replication and VEE infection. See Durbin et al., *Vaccine* 16:1234-1330 (1999). Table 1 shows the virus titers obtained in LRT and URT after immunization and challenge. All the VRPs that expressed either NP, P, M, or C at doses ranging from $1 \times 10^6$ to $1 \times 10^7$ i.u given i.n. or i.m. showed no obvious protection as compared to VRP-GFP and PBS groups (Table 1). Only cp45, which is a live attenuated PIV3 virus, was able to protect hamsters from PIV3 infection. Therefore, it was concluded that internal proteins NP, P, M, and C had very minimal or no efficacy as candidates for inclusion in immunogenic compositions against PIV3.

The ability of VRP-expressed HN and/or F to provide protection was then investigated. Hamsters were immunized according to the same schedule and at the doses indicated in Table 2. The results, shown in Table 2 indicate that only VRP-F/HN immunized animals were almost completely protected in the URT. Hamsters immunized with VRP-HN alone had decreased viral titers by around 100-fold in the URT. Immunization of hamsters with VRP-HN+VRP-F i.n., rather than VRP-F/HN, decreased viral replication in URT by only 10-fold. Further, VRP-F immunization elicited no serum neutralizing titers and no protection in the URT, and only 10-fold reduction of viral replication in the LRT (Table 2, expt. 1). Therefore, by i.n. immunization, the immunogenic composition comprising VRP-F/HN induced significant levels of neutralizing titers, as well as the complete protection against PIV3 infection in the LRT, and reduced severity of PIV3 infection in the URT.

TABLE 2

Coexpression of HN and F simultaneously in the same VRP provided the best protection against PIV3 infection

| Expt. | Immunization | Dose (iu) | Route | Serum HI (Log2) (reciprocal of dilution) | Viral Titers (−logTCID50/ml) LRT | URT |
|---|---|---|---|---|---|---|
| Expt. 1 | VRP-HN | $1 \times 10^5$ | i.n. | 6.3 ± 0.6 | 0 | 2.9 ± 0.7 |
|  | VRP-F | $1 \times 10^5$ | i.n. | 0 | 4.0 ± 0.7 | 5.1 ± 0.1 |
|  | VRP-HN + VRP-F | $(1 + 1) \times 10^5$ | i.n. | 7.5 ± 0.4 | 0 | 4.3 ± 0.2 |
|  | VRP-F/HN | $1 \times 10^5$ | i.n. | 7.1 ± 0.1 | 0 | 1.4 ± 0.8 |
|  | PBS | 100 ul | i.n. | 0 | 5.8 ± 0.4 | 5.2 ± 0.2 |
|  | VRP-HN | $1 \times 10^5$ | i.m. | 6.2 ± 0.5 | 2.5 ± 1.0 | 3.7 ± 0.5 |
|  | VRF-F | $1 \times 10^5$ | i.m. | 0 | 5.1 ± 0.1 | 4.2 ± 0.5 |
|  | VRP-HN + VRP-F | $(1 + 1) \times 10^5$ | i.m. | 4.8 ± 1.0 | 2.9 ± 1.2 | 5.5 ± 0.1 |
| Expt. 2 | VRP-F/HN | $1 \times 10^5$ | i.m. | — | 0 | 4.4 ± 0.4 |
|  | VRP-HN + VRP-F | $(1 + 1) \times 10^5$ | i.m. | — | 3.1 ± 0.5 | 5.8 ± 0.1 |
|  | PBS | 100 ul | i.m. | — | 6.1 ± 0.1 | 6.1 ± 0.0 |

In general, intramuscular immunization was less effective than intranasal immunization in eliciting protective immunity against PIV3. For example, animals that were immunized intramuscularly (i.m.), with VRP-HN and VRP-HN+VRP-F showed reduced viral titers in LRT by around 3 $\log_{10}$ (Table 2, expt. 1), as compared to intranasal immunization with these replicons, which produced complete protection from subsequent challenge infection in the LRT.

Again, the most effective immunogenicity was obtained with VRP-F/HN, which accorded complete protection from subsequent challenge infection in the LRT (Table 2, expt. 2) for both i.m. and i.n. immunization. No examples of complete protection were achieved by i.m. immunization using VRPs other than VRP-F/HN (Table 2).

The data showed a range of protection in the form of reduced viral titers and reduced severity of infection is possible in the URT through i.m. immunization. Specificially, intramuscular immunization using VRP-HN, VRP-F, VRP-HN+VRP-F, resulted in reductions in virus titers by a range of about 10-fold to about 100-fold as compared to PBS control (Table 2, expt. 1 & 2). VRP-F/HN was the best candidate to protect against LRT infection when given i.m., although less efficacious than i.n. immunization.

Example 4

Humoral Responses to PIV

A. PIV3-specific B Cell ELISPOT:

PIV3 specific Ig secreting cells in the lymph nodes of mice were measured by B cell ELISPOT assay. Briefly, single cell suspensions from lymph nodes of immunized mice were incubated onto 96-well Immulon II plates (Millipore, Bedford, Mass.) that were coated with 100 ng of detergent disrupted PIV3 virus overnight at 37° C. in 5% $CO_2$. Cells were then washed off and PIV3-specific total Ig or IgA bound to the plates were detected by a mixture of alkaline phosphatase conjugate goat anti-mouse IgM+IgG+IgA or IgA only, respectively. Spots were then developed by using an alkaline phosphatase substrate kit (Bio-Rad) and quantified by counting under an Olympus dissecting microscope (Leeds Precision Instruments, Inc., Minneapolis, Minn.). The results are reported as the number of Spot Forming Cells (SFC) per $1 \times 10^6$ cells.

B. Viral Neutralization Assay:

The ability of hamster sera to neutralize PIV3 virus particles was measured by hemaglutination inhibition assay (HI). Briefly, heat inactivated sera were treated with receptor destroying enzyme (RDE) (Denka Seiken Co. Ltd., Tokyo, Japan) for 18-20 hours at 37° C. to remove non-specific inhibitors prior to further removal of non-specific agglutinin by incubating with 0.4% guinea pig RBCs (gpRBCs) at 4° C. for 1 hour. The endpoint of serially diluted treated sera to inhibit 4 HA unit of PIV3 virus to agglutinate 0.5% gpRBCs was then determined.

The demonstrated protective efficacy of VRP-F/HN led to an investigation of its protective effects. Protection from respiratory pathogens is generally associated with induction of mucosal immunity. Therefore, the induction of IgA producing cells in the mediastinal lymph nodes (MLNs) and the cervical lymph nodes (CLNs), which drain either the lungs or the nose, was assessed. In this case a mouse model was used because an appropriate detection reagent for hamsters was unavailable. BALB/c mice were immunized with VRP-HN, or VRP-F/HN (i.n.) according to the same immunization schedule for hamsters. Individual CLNs were collected and MLNs were pooled. Single cell suspensions were prepared from the LNs and total Ig secreting cells or IgA secreting cells were analyzed by B cell ELISPOT technique.

Immunization with VRP-F/HN induced higher levels of antigen specific IgA as compared to immunization with other VRPs. For example, immunization with VRP-HN induced about 800 SFCs per $1 \times 10^6$ cells of PIV3-specific Ig secreting cells in the CLNs. Out of these only approximately 10% of these Ig secreting cells were PIV-3 specific IgA secreting cells (less than 100 SFCs per $1 \times 10^8$ cells). In contrast, VRP-F/HN immunization induced about 400 SFCs per $1 \times 10^6$ cells of PIV3-specific Ig-SFCs in the CLNs. Importantly, the number of antigen specific IgA SFCs was much higher on a percentage basis than with VRP-HN (about 250 SFCs per $1 \times 10^6$ cells). In this case, more than 60% of Ig the secreting cells in the VRP-F/HN immunization groups were IgA. Therefore, VRP-F/HN preferentially induced antigen specific IgA production in URT and this correlated with a better protection efficacy (Table 2).

In the MLNs, amounts of PIV3-specific total Ig secreting cells or IgA secreting cells were similar for both VRP-HN and VRP-F/HN immunization, consistent with the fact that both immunizations completely cleared viral replication in the LRTs of hamsters (Table 2).

The role of neutralizing antibodies in protective immunity following virus challenge was investigated. Serum samples were collected two days before PIV3 challenge and PIV3 neutralization titer was measured. Table 2 shows that no neutralizing titer was detected in a PBS control group and viral replication in LRT and URT was up to level of 5.8±0.4 and 5.2±0.2, respectively. Among all the experimental groups, VRP-HN, VRP-F/HN, or a combination of VRP-HN and VRP-F (VRP-HN+VRP-F) immunization induced significant levels of Hi titers, reaching levels of 6.3, 7.1, and 7.5, respectively, comparable to that of cp45 immunized group (data not shown) and showed full protection in the LRT.

Example 5

Minimal Dose for PIV Protection

The minimal dose for VRP-F/HN immunization necessary for effective protection was assessed. VRP-F/HN at dose of $2 \times 10^4$ iu when given i.n. could still protect LRT from infection and afford partial protection against URT infection by lowering viral replication by 100-fold (Table 3, Expt. 1). Further, the third injection seemed to be unnecessary and two injections of a $1 \times 10^4$ i.u. dose was sufficient to prevent LRT infection. One dose of VRP-F/HN $1 \times 10^4$ iu was not sufficient (Table 3, expt.2). Therefore, in the hamster model, VRP-F/HN was the most effective regimen to prevent establishment of PIV3 replication in the lower and upper respiratory tracts. The dosage for VRP-F/HN as effective to combat LRT infection could be as low as two immunizations at $1 \times 10^4$ iu.

The data indicated that immunization with two doses of $1 \times 10^4$ iu of VRP-F/HN was sufficient to reduce virus replication to undetectable levels in LRT and decreased the level of virus replication by about 100-fold in URT (Table 3). This is a significant achievement, because it suggests a way to prepare a subunit composition capable of preventing certain disease complications such as PIV and RSV associated pneumonia. The data show that HN and F are the two critical antigens needed for PIV3 subunit vaccine design.

TABLE 3

VRP-F/HN I.N Immunization Was Very Potent In LRT Protection

| Expt. | Immunogen | Dose (No. of doses) | Viral Titers (−logTCID50/ml) | |
|---|---|---|---|---|
| | | | LRT | URT |
| Expt. 1 | VRP-F/HN | $2 \times 10^4$(3) | 0 | $3.6 \pm 0.1$ |
| | | $2 \times 10^3$(3) | $5.5 \pm 0.1$ | $5.6 \pm 0.1$ |
| | | $2 \times 10^2$(3) | $5.8 \pm 0.1$ | $5.7 \pm 0.2$ |
| | PBS | 100 ul | $6.1 \pm 0.1$ | $6.1 \pm 0.0$ |
| Expt. 2 | VRP-F/HN | $1 \times 10^4$(3) | 0 | $3.3 \pm 0.5$ |
| | | $1 \times 10^4$(2) | 0 | $4.7 \pm 0.3$ |
| | | $1 \times 10^4$(1) | $4.3 \pm 0.1$ | $2.5 \pm 1.2$ |
| | PBS | 100 ul | $5.4 \pm 0.2$ | $4.9 \pm 0.3$ |

Example 6

Cytopathic Effects from VRP-F/HN Infection

A. Apoptosis

The potent efficacy of VRP-F/HN as an immunogenic composition when compared to VRP-HN, VRP-F, or VRP-HN+VRP-F led to an investigation of the mechanism of action. It was observed that VRP-F/HN infection led to a unique CPE, compared to other VRP infections in culture. The ability of these VRPs when propagated in culture to lead to apoptosis was investigated. BHK21 monolayers were infected with VRP-F/HN or VRP-HN at MOI=0.5, or not infected (as controls). See Table 4. Monolayer morphology was observed under phase contrast microscopes with amplification 100× at 24, 48, and 72 hours after infection. See Table 4. The CPE data were characterized by whether the BHK monolayers were disorganized showing mild CPE (+), or whether monolayers cells were severely destroyed and whether membrane blebs were formed (++) or whether the monolayers were completely wiped off, leaving blebs and debris (+++) in supernatant. See Table 4.

As shown in Table 4, when BHK cells were infected with VRP-F/HN, 24 hours later, BHK monolayers were disorganized as compared to VRP-HN or other VRPs (data not shown) infection. After 48 hours, infection with VRP-F/HN induced monolayer destruction, and obvious syncytium and membrane blebs were formed. By 72 hours, monolayers were completely wiped off, leaving blebs and debris in the supernatant, while the VRP-HN infected group showed intact monolayers with cells rounding up due to apoptosis events throughout. See Table 4.

TABLE 4

Degree of CPE in Replicon Infected Cells

| Groups | CPE | | |
|---|---|---|---|
| | 24 Hours | 48 Hours | 72 Hours |
| Uninfected | − | − | − |
| VRP-F/HN | + | ++ | +++ |
| VRP-HN | − | − | − |

B. Plaque Morphology

Previous studies have shown that the fusion properties of F protein require the presence of HN protein (Ebata, S. N. et al. Virology 183:437-441 (1991)) while by themselves neither HN nor F could induce syncytial formation. The possibility that the unique CPE by VRP-F/HN infection was due to syncytial formation was next examined.

BHK21 monolayers of cells were infected with different VRPs, for example, VRP-HN, VRP-F, VRP-HN+VRP-F or VRP-F/HN, for 15-18 hours and monolayers were then fixed and stained with horse anti-PIV3 polyclonal Ab and then horseradish peroxidase conjugated anti-horse Ab as secondary Ab plus aminoethylcarbazole peroxidase as substrate; or with rabbit anti-VEE NSP1 polyclonal Ab r835 plus cyTM3 conjugated goat anti-rabbit antibody. Pictures were taken under bright field or fluorescence microscope with amplification of 100×.

As expected, VRP-HN or VRP-F by itself showed clearly HN- or F-expression plaques formed by individual VRP infection. However, "plaques" in the VRP-F/HN infected group had much larger size and could be visualized easily. These larger "plaques" actually represented the formation of syncytia because multinucleated cells were clearly seen within these "plaques" [titration based on syncytium formation was later called syncytial forming unit (sfu) instead of infectious unit (iu) since it was based on single replicons and multiple cells]. When cells were coinfected with VRP-HN and VRP-F simultaneously, there were fewer "plaques" (less than 1%) which showed syncytial morphology. However, the plaques were similar to those formed by VRP-HN or VRP-F infection alone. The same plaque profile was seen when plaques were stained with anti-VEE NSP1 Ab. The syncytial formation also further confirmed the co-expression of HN and F proteins from VRP-F/HN. It was concluded that VRP-F/HN infection in fact led to two different CPE processes, apoptosis and syncytia formation.

Example 7

Coexpression of HN and F Produced Infectious Particles

It was noticed that the VRP-F/HN induced CPE was very "contagious," because monolayers of cells ("monolayers") would be destroyed by very low multiplicities of infection (MOI) (<0.001, data not shown). Therefore, it was surmised that some form of secondary replicons or infectious particles were being generated from the unique CPE. These secondary replicons or infectious particles appeared to be self-propagating and infecting other cells by using membrane associated HN and F glycoprotein induced fusion processes.

In order to evaluate whether there were non-replicon infectious agents being produced, experiments were designed in which BHK monolayers were infected with VRP-F/HN or other VRPs at a MOI of 0.5 for 30 minutes. The monolayers were then washed three times to remove any residual VRPs, replenished with fresh media and cultured for 48 hours. Next, the monolayers were stained with horse anti-PIV3 sera to assess for HN and F expression, or with rabbit anti-NSP1 of VEE to determine the presence of replicon NSP1 protein. At the end of the 48 hour time period, aliquots of the supernatants from the cells were removed from the monolayers and used to "infect" fresh BHK monolayers for 30 minutes. After 30 minutes the cells were washed, replenished with fresh media and incubated for 48 hours. The monolayers were then evaluated for CPE and stained with horse anti-PIV3 sera for HN and F expression, or with rabbit anti-NSP1 of VEE to determine the presence of replicon proteins. The procedure was carried out through first transfer ($1^{st}$ transfer), another transfer ($2^{nd}$ transfer), and a transfer ($3^{rd}$ transfer). All cells were stained with either anti-PIV3 for HN and F expression or anti-VEE NSP1 for VEE NSP1 expression. Photos were taken with amplification of 100× under bright field for anti PIV antibodies, or fluorescence microscope for anti VEE NSP1 antibodies. The magnitude of expression by immunostaining is denoted by (−) or (+) through (+++++). The results are shown in Table 5.

TABLE 5

Infectivity of Supernatants From Replicon Infected Cells

| Antibody | Presence of Antigens From Replicon | | | |
|---|---|---|---|---|
| | VRP-HN | VRP-F | VRP-HN + VRP-F | VRP-F/HN |
| Horse Anti-PIV serum | ++ | + | ++ | ++++ |
| Anti-PIV 3-1$^{st}$ transfer | − | − | + | +++++ |
| Anti-PIV3-2$^{nd}$ transfer | − | − | − | +++++ |
| Anti-PIV3-3$^{rd}$ transfer | − | − | − | +++++ |
| Anti-VEE NSP1 Ab | + | + | + | +++ |
| Anti-VEE NSP1 Ab - 1$^{st}$ transfer | − | − | − | +++++ |
| Anti-VEE NSP1 Ab - 2$^{nd}$ transfer | − | − | − | +++++ |
| Anti-VEE NSP1 Ab - 3$^{rd}$ transfer | − | − | − | ++++ |

In the first round of infection with VRP replicons, plaques were visible after 48 hours in cell lines infected with the following replicons: VRP-HN, VRP-F, and VRP-HN+VRP-F. See Table 5. In this round of infection, VEE glycoproteins that were derived from helper plasmids facilitated cell entry.

Considering CPE in the initial replicon infection, the VRP-HN+VRP-F infected cells showed occasional syncytial formation due to opportunistic coexpression of HN and F. In contrast, VRP-F/HN infection after 48 hours induced destruction of cell monolayers and obvious syncytium. See Table 5. All of these groups also expressed VEE NSP1 proteins, indicating active replicon activities. See Table 5.

In the second round of infection, when the above supernatants were transferred to new monolayers, there were no new infection activities in the VRP-HN and VRP-F treated groups. See Table 5. Similiarly, there was no further expression of PIV3 HN and F, nor was there any VEE NSP1 production. See Table 5. In these groups, the absence of an input of VEE helper proteins proved fatal to the infection process as would be expected prior to the present invention.

Surprisingly, however, infectious particles were being produced in the supernatants of VRP-F/HN treated cells in the absence of VEE proteins on the helper plasmids. For example, we found large amounts of PIV3 glycoproteins HN and F being produced following transfer of supernatant from VRP-F/HN treated cells to uninfected cell monolayers. See Table 5. At this stage in the process, it was thought that the infection process was driven by the surface expressed fusion activity of PIV HN and F proteins on the surface of cell derived blebs.

In addition, NSP1 proteins were detected being produced in the VRP-F/HN treated group following the transfer, indicating strong infectious activities in the VRP-F/HN infected cell supernatants. See Table 5. VEE surface glycoprotein expression was undetectable using staining with anti-VEE polyclonal serum, thus indicating no VEE virus generation due to a potential recombination event. Therefore, the infectious agent is comprised of the original VEE replicon RNA, which carries VEE replicase comprising NSP1, NSP2, NSP3, NSP4, and PIV3 HN and F genes. In addition, we show here that these same proteins are being expressed.

The infectious activity in subsequent transfers appeared driven by co-expression of PIV3 HN and F. There was a limited amount of PIV3 glycoprotein HN and F antigen staining and no detectable NSP1 expression in the VRP-HN+VRP-F group. See Table 5. The reason for this may be that some replicons with syncytium inducing activity were carried over from the initial VRP infection. See Table 5. In support of this, it was found that this residual activity was unable to carry over with the second transfer and no further PIV3 antigen was detected. See Table 5.

In contrast to the lack of infectious activity seen with of VRP-HN+VRP-F treated cells, supernatants from cells receiving the first transfer of VRP-F/HN infection could, when applied to uninfected cells, induce another round of "infectious" phenomena including syncytial formation, monolayer disruption, PIV3 HN & F antigen staining and VEE NSP1 antigen staining. Again, there was no detectable VEE surface glycoprotein expression as a result of these infectious activities, further ruling out VEE virus contamination.

Further rounds of "infectious" phenomenon were produced when supernatants from VRP-F/HN infected cells were transferred to additional BHK monolayers. See Table 5. BHK monolayers were also stained with anti-VEE polyclonal serum and showed no VEE surface protein expression, indicating no VEE virus generation.

The above observations further confirmed the hypothesis that there were "infectious" protein driven fusogenic activities generated from VRP-F/HN infected cells, and these activities could be continuously transferred.

Example 8

Infectious Particles were Blebs not Replicons

The morphological nature of the infectious particles was examined using an electron microscope in order to ascertain their nature. Closer examination ruled out that the infectious particles were VRP-F/HN replicons, and instead identified the infectious agents as blebs derived from infected cells, which co-express PIV3 HN and F.

VRP-F/HN blebs were prepared for electron microscopy by first diluting them 1:20 in PBS. Whole bleb, negative stain, immunogold labeling was performed using a modified procedure developed by Slot and Geuze 1984. See Immunolabeling for Electron Microscopy, by Slot and Geuze, Pollack and Varndell eds. Elsevier Science Publishers, BV, Amsterdam. Droplets of vesicles were placed on parafilm and formvar-carbon-coated gold grids were placed face down on each droplet. Excess fluid was wicked off and blocking was accomplished in two stages using PBS and 1% BSA (5 ml) and later, PBS containing 1% cold water fish gelatin (10 ml). Grids, with blebs, were inverted over anti-F mAb clone B-102 or anti-HN mAb clone 68/2 diluted 1:50 in PBS BSA (1 h) in a humid chamber. Grids were rinsed 5×1 ml in PBS BSA. Antigen was detected by incubation with goat anti-mouse IgG+M conjugated to 6 nm colloidal gold beads, (Jackson ImmunoResearch Labs, W. Grove, Pa.). Rinsing took place in PBS (4×1 ml). Grids with cells were stabilized with 1% glutaraldehyde in PBS (3 ml). Each sample was then rinsed in distilled water (5×1 ml). Finally, grids with vesicles were negatively stained (30 s) using 1% PTA, pH 6.5. Control samples were incubated in the absence of primary antibody. Examination took place on a Zeiss 10C transmission electron microscope operating at 80 kV.

Electron microscopy studies of a sample of infectious particles from supernatants indicated that the infectious particles were not VRP-F/HN replicons. VEE replicons are 70 nm virus particles closely approximating VEE virus in size. See Paredes et al., *J. Virol.* 75:9532 (2001). Negative staining revealed a significant amount of heterogeneity in size. In contrast, VEE replicons are known to be homogenous in size.

The infectious particles displayed surface expression of PIV3 HN and F glycoproteins, which was inconsistent with VRP-F/HN replicons as the infectious material. The purified infectious particles were subjected to immunogold labeling using anti-HN monoclonal antibody "clone 68/2" and anti-F monoclonal antibody "clone B-102." The results showed that infectious particles were predominantly stained with anti-HN and anti-F, as compared to control stained with murine Ig isotype. This result further confirmed that the infectious material was not replicon based, because only VEE glycoproteins would be expressed on the surface of a replicon. According to the packaging properties of VEE replicons, PIV3-HN and F glycoproteins would be excluded from replicon particle. See Straus, J. H. & Strauss E. G., The Alphaviruses: Gene Expression, Replication and Evolution. *Microbiological Reviews* 58(3):491-562 (1994), the disclosure of which is hereby incorporated by reference in its entirety.

Example 9

Infectivity of Infectious Blebs Mediated by HN and F

The identity of surface proteins meditating cellular entry of these infectious blebs was evaluated by assessing whether antibodies to specific proteins could inhibit infectivity. First, infectious blebs or VEE replicons that encode GFP were preincubated with various antibodies such as Anti-PIV3 serum; Anti-HN mAb; Anti-F mAb; Anti-HN mAb+Anti-F mAb; normal serum and isotype control murine Ig for two hours. Next, BHK monolayers were infected for 1 hour with these preincubated infectious blebs or VEE replicons. Monolayers were then washed and replaced with growth media. Infection by blebs was determined by fixing the cells and staining with rabbit anti-VEE NSP1 and cyTM3conjugated goat anti-rabbit antibody overnight. Infection by VEE replicons were viewed by expression of green fluorescence proteins after 5 hour culture. Pictures were taken under fluorescence microscope with amplification of 100×. Evidence of magnitude of infection was scored in Table 6 as (+), or (++). A lack of evidence of infection was scored as (−).

TABLE 6

Inhibition of Bleb Infectivity by Anti PIV Antibodies

| Preincubation Antibody | Inhibition of Infectivity | |
| --- | --- | --- |
| | Blebs | replicons |
| Anti-PIV3 serum | − | ++ |
| Anti-HN mAb | − | ++ |
| Anti-F mAb | + | ++ |
| Anti-HN mAb + Anti-F mAb | − | ++ |
| Anti-VEE mAb | ++ | − |
| Normal serum | ++ | ++ |
| Isotype control murine Ig | ++ | ++ |

The data shown in Table 6 indicate that pre-incubation of infectious blebs with anti-PIV3 polyclonal antiserum or monoclonal antibodies to PIV3 HN completely blocked the ability of the blebs to self-propagate or infect new cells. When blebs were incubated with a single monoclonal antibody to the fusion protein of PIV3, infectivity was somewhat diminished, but not totally inhibited. Pre-incubation of blebs with a monoclonal antibody to VEE proteins had no effect on bleb infectivity.

The effect of antibody preincubation on subsequent infectivity was very different when replicons were used rather than blebs. For example, neither polyclonal antiserum to PIV3 nor monoclonal antibodies to PIV3 glycoproteins HN and F could inhibit VRP-HN/P infectivity. See Table 6. In contrast, only pre-incubation with a monoclonal antibody to VEE surface glycoproteins could inhibit VRP-F/HN infectivity.

Several important points can be drawn from these studies of antibody inhibition of infectivity. First, the infectivity inhibition results indicated that the HN and F proteins were located on the surface of the self-propagating blebs. The results further indicated that the self-propagating activity that appeared to be infectivity is driven by the fusogenic glycoproteins PIV3 HN and F located on the surface of the self-propagating blebs. In contrast, these results confirmed that it was the VEE structural proteins E1 and E2, which bind to receptors and drive the first round of infection when replicons are used to infect cells.

Example 10

Amplification of Infectious Blebs Versus Replicons

Next, it was investigated whether these infectious, self propagating blebs could be amplified like a virus and how this such amplification compared to the growth characteristics of the original replicons. To do this, first the VRP-F/HN replicons were amplified as follows: (i) T-175 flasks of subconfluent BHK cells were infected with about $1 \times 10^5$ iu (sfu) of VRP-F/HN for 1 hour; (ii) then the cells were washed and replaced with fresh media; and (iii) syncytia forming activity was monitored over time using the same protocol for VRP-F/HN titration. It was found that in the first 16 hours, there was a low titer of infectious activity present (~300 sfu). Syncytia were formed during the titration procedure, which displayed similar morphology as those of VRP-F/HN. Approximately forty hours later, syncytia forming activities increased dramatically by almost 2500-fold and remained unchanged for another 72 hours. Therefore the burst size for the replicon particles was calculated as about 0.1.

In comparison, the ability of "infectious bleb particles" produced from VRP-F/HN infected cells to be amplified like replicons was examined. Again T-175 flasks of BHK cells were used, at about 80% confluency, which were infected with about $1 \times 10^4$ sfu of self-propagating blebs in the form of culture supernatant of VRP-F/HN infected cells for 1 hour. Then the cells were washed and replaced with fresh media and syncytia forming activity was monitored over time. Amplification of self-propagating blebs as measured by syncytia forming activity was better than amplification of VRP-F/HN replicons. The growth curve for self-propagating blebs showed low titers (~500 sfu) for the first 16 hours and was followed by a drastic increase in syncytial forming activity by 560-fold in the first 40 hours. Subsequently, at about 112 hours after initial infection, the titer of syncytia forming activity had increased up to approximately 15,000-fold. This data further supported the idea that VRP-F/HN infection produces infectious particles, which are termed self-propagating blebs, which could further autonomously propagate. These secondary "infectious bleb" particles could only be generated from VRP-F/HN infection, but not from VRP-HN, VRP-F, or VRP-HN+VRP-F. This phenomenon might further explain the effective priming of appropriate protective immunity and the potency of VRP-F/HN as candidates for immunogenic compositions against PIV3 infection.

Example 11

Characterization of Infectious Blebs

The possible fragility of self-propagating blebs was examined in response to typical physical phenomena such as freeze-thaw, vortexing, freezing to −80° C. for 7 days, centrifugation at 2500 rpm for 20 minutes, and filtration through 0.2 µm, 0.45 µm, and 0.8 µm filters. The blebs were titered before and after subjecting them to each physical test and the results are shown in Table 7 below.

These results indicated that physically the infectivity of the blebs was robust when confronted with everyday phenomena such as freezing, vortexing, and centrifugation. Interestingly, the infectivity is greatly enhanced by vortexing, perhaps because there is some stickiness or clumping of the blebs that is broken up by vortexing. The filterability of the infectivity supports the notion that there is some tendency of the blebs to clump.

TABLE 7

Fragility of Bleb Infectivity

| Physical Treatment | Titer (sfu × $10^{-4}$/ml) |
|---|---|
| None | 3.06 |
| Freeze-thaw | 2.79 |
| Vortexing for 2 minutes | 9.81 |
| Freezing to −80 C. for 7 days | 2.30 |
| Centrifugation at 2500 rpm for 20 min: Supernatant | 2.75 |
| Centrifugation at 2500 rpm for 20 min: Pellet | 2.03 |
| Filtration through 0.2 µm | 0.47 |
| Filtration through 0.45 µm | 1.1 |
| Filtration through 0.8 µm | .88 |

Example 12

Immunization Using Infectious Blebs

A. Self-Propagating, Infectious Blebs Protected Hamsters from PIV3 Infection

Table 8 shows the results from an experiment where hamsters were vaccinated with either VRP-F/HN or supernatants from VRP-F/HN infected BHK cells (Blebs). The VRP-F/HN were given either 1, 2 or 3 inoculations. See Table 8. The blebs were administered either 1, 2 or 3 times intranasally. The doses are indicated in Table 8 as 1st dose $2.8 \times 10^4$; $2^{nd}$ dose at $2.6 \times 10^3$; and 3rd dose at $1 \times 10^5$ sfu. Animals were all challenged with $1 \times 10^6$ LogTCID50 of PIV3 virus at 7 weeks after the initial immunization and viral replication in respiratory tracts was analyzed. Data were reported as average±SEM (n=4-6).

The results in Table 8 demonstrated, that hamsters immunized with VRP-F/HN replicons required three doses to elicit the same Hi titer as compared to hamsters immunized with VRP-F/HN infected BHK cells (Blebs), which only required two doses. Furthermore, two doses of Blebs were sufficient to clear the virus in LRT and URT, whereas, hamsters immunized with two doses of VRP-F/HN replicons only cleared in the LRT. (See Table 8).

TABLE 8

Inoculation with Blebs Protects From PIV Infection

| Vaccine Candidates | Dose (#of Dose) | Serum HI 1/dilution (−log 2) | Viral Titers (log TCID50/ml) | |
|---|---|---|---|---|
| | | | LRT | URT |
| VRP-HN/F | $1 \times 10^4$ (3) | 6.3 ± 0.3 | 0 | 3.3 ± 0.5 |
| | $1 \times 10^4$ (2) | 4.8 ± 0.3 | 0 | 4.7 ± 0.3 |
| | $1 \times 10^4$ (1) | 0 | 4.3 ± 0.1 | 2.5 ± 1.2 |
| Blebs (SNP) | | | | |
| 3 doses | $2.8 \times 10^4$, ($1^{st}$) $2.6 \times 10^3$, ($2^{nd}$) $1 \times 10^5$ ($3^{rd}$) | 7.3 ± 0.3 | 0 | 0 |
| 2 doses | $2.8 \times 10^4$, ($1^{st}$) $2.6 \times 10^3$ ($2^{nd}$) | 6.8 ± 0.6 | 0 | 0.6 ± 0.6 |
| 1 dose | $2.8 \times 10^4$ ($1^{st}$) | 0.38 ± 0.6 | 3.9 ± 0.4 | |
| cp45 | $1 \times 10^5$ | 6.6 ± 0.2 | 0 | 0 |
| PBS | 100 µl | 0 | 5.4 ± 0.2 | 4.9 ± 0.3 |

Since, two doses seemed to be the optimal dose for protection for animals with the VRP-F/HN (Blebs), the optimal route was evaluated for total protection in hamsters. In this set of studies, shown in Table 9, hamsters were immunized with two doses of blebs that contained the same HN protein concentration (0.58 ng) (for VRP-HN-, or VRP-F/HN-infected supernatants) and/or the same F (0.21 ng) concentration (for VRP-F- or VRP-F/HN-infected supernatants) either intranasally (IN) or intramuscularly (IM). All the inoculants showed 0 sfu except supernatants from VRP-F/HN infected culture, which contained infectious bleb activities equal to 7000 sfu per dose. See Table 9. Animals were then challenged intranasally with $1 \times 10^5$ LogTCID$_{50}$ of PIV3 virus at 7 weeks after the last immunization and viral replication in respiratory tracts, and neutralization titers were analyzed. Data were reported as average±SEM (n=4-6).

TABLE 9

Blebs Protected Using Different Routes of Administration

| Immunogen | Dose: # of doses | Serum HI 1/dilution (−log2) | Viral Titers (−log TCID$_{50}$/ml) | |
|---|---|---|---|---|
| | | | URT | LRT |
| V-HN SNP (IN) | 2 | 1.5 ± 0.96 | 5.20 ± 0.08 | 4.00 ± 0.18 |
| V-F-SNP (IN) | 2 | 2.8 ± 0.11 | 4.67 ± 0.17 | 4.72 ± 0.29 |
| V-HN + V-F SNP (IN) | 2 | 1.0 ± 0.63 | 5.00 ± 0.09 | 4.39 ± 0.23 |
| V-F/HN SNP (IN) | 2 | 6.4 ± 1.69 | 1.89 ± 0.85 | 0.00 ± 0.00 |
| V-HN SNP (IM) | 2 | 5.2 ± 1.05 | 5.17 ± 0.24 | 3.22 ± 0.49 |
| V-F-SNP (IM) | 2 | 0.7 ± 0.42 | 4.83 ± 0.14 | 4.11 ± 0.29 |
| V-HN + V-F SNP(IM) | 2 | 3.0 ± 1.37 | 4.87 ± 0.13 | 3.53 ± 0.23 |
| V-F/HN SNP (IM) | 2 | 8.0 ± 0.96 | 4.89 ± 0.23 | 0.00 ± 0.47 |
| cp45-IN | 2 | 9.7 ± 0.56 | 0.00 ± 0.00 | 0.00 ± 0.00 |
| PBS-IN | 1 | 1.2 ± 0.75 | 4.53 ± 0.28 | 3.94 ± 0.23 |

The results demonstrated that VRP-F/HN infected BHK cells (Blebs) given by the intranasal route, cleared the virus in both upper and lower respiratory tract but, when given by the intramuscular route only cleared in the lower respiratory tract (LRT). Animals immunized with supernatants from replicon infected cells that contained VRP-HN, or VRP-F, or VRP-HN+VRP-F did not clear the virus from LRT and URT.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated recombinant Venezuelan Equine Encephalitis nucleic acid replicon molecule encoding a Venezuelan Equine Encephalitis virus replicase, a parainfluenza virus type 3 F glycoprotein, and a parainfluenza virus type 3 HN glycoprotein.

2. An isolated recombinant Venezuelan Equine Encephalitis nucleic acid replicon molecule encoding a Venezuelan Equine Encephalitis virus replicase, a parainfluenza virus type 3 F glycoprotein, and a parainfluenza virus type 3 HN glycoprotein having the nucleic acid sequence shown in SEQ ID NO: 1.

3. An immunogenic composition comprising a population of Venezuelan Equine Encephalitis virus replicon particles (VRP) comprising Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene.

4. The immunogenic composition of claim 3, wherein said Venezuelan Equine Encephalitis virus replicon particles induce cytopathic effects when used to infect monolayers of BHK cultured cells.

5. The immunogenic composition of claim 4, wherein supernatants from cells infected with said replicon particles, when transferred to uninfected cell monolayers induce said cytopathic effects in the absence of said replicon particles.

6. The immunogenic composition of claim 4, wherein said cytopathic effect in BHK cultured cells is syncytia formation.

7. The immunogenic composition of claim 4, wherein said cytopathic effect in BHK cultured cells is monolayer disruption.

8. The immunogenic composition of claim 4, wherein said population contains no detectable replication competent Venezuelan Equine Encephalitis virus.

9. An immunogenic composition comprising a population of Venezuelan Equine Encephalitis virus replicon particles (VRP) comprising Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;
   wherein said population contains no detectable replication competent Venezuelan Equine Encephalitis virus;
   wherein said replicon particles induce cytopathic effect when used to infect monolayers of cultured BHK cells;
   and wherein supernatants from cells infected with said replicon particles, when transferred to uninfected cell monolayers induce said cytopathic effects in the absence of said replicon particles.

10. An immunogenic composition comprising a population of Venezuelan Equine Encephalitis virus replicon particles (VRP) comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;
   wherein said population contains no detectable replication competent Venezuelan Equine Encephalitis virus;
   wherein said replicon particles induce cytopathic effect when used to infect monolayers of cultured BHK cells;
   wherein supernatants from cells infected with said replicon particles, when transferred to uninfected cell monolayers induce said cytopathic effects in the absence of said replicon particles;
   and wherein said Venezuelan Equine Encephalitis virus replicon particles elicit a protective immune response in a mammalian host.

11. An immunogenic composition comprising a population of Venezuelan Equine Encephalitis virus replicon particles (VRP) comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene and where the replicon vector comprises the nucleic acid sequence shown in SEQ ID NO: 1;
   wherein said population contains no detectable replication competent Venezuelan Equine Encephalitis virus;
   and wherein supernatants from cells infected with said replicon particles when transferred to uninfected cell monolayers induce said cytopathic effects in the absence of said replicon particles.

12. An immunogenic composition comprising a population of Venezuelan Equine Encephalitis virus replicon particles (VRP) comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene and where the nucleic acid portion of the replicon vector comprises the nucleic acid sequence shown in SEQ ID NO: 1;
   wherein said population contains no detectable replication competent Venezuelan Equine Encephalitis virus;
   wherein supernatants from cells infected with said replicon particles, when transferred to uninfected cell monolayers induce said cytopathic effects in the absence of said replicon particles;
   and wherein said Venezuelan Equine Encephalitis virus replicon particles elicit a protective immune response in a mammalian host.

13. An immunogenic composition comprising Venezuelan Equine Encephalitis virus replicon particles (VRP) comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene and where the replicon vector comprises the nucleic acid sequence shown in SEQ ID NO: 1;
  wherein said population contains no detectable replication competent Venezuelan Equine Encephalitis virus;
  wherein said Venezuelan Equine Encephalitis virus replicon particles elicit a protective immune response in a mammalian host;
  wherein said replicon particles induce cytopathic effect when used to infect monolayers of cultured BHK cells;
  and wherein supernatants from cells infected with said replicon particles, when transferred to uninfected cell monolayers induce said cytopathic effects in the absence of said replicon particles.

14. An immunogenic composition comprising a population of Venezuelan Equine Encephalitis virus replicon particles (VRP) comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;
  wherein said population contains no detectable replication competent Venezuelan Equine Encephalitis virus;
  wherein supernatants from cells infected with said replicon particles, when transferred to uninfected cell monolayers induce cytopathic effects in the absence of said replicon particles;
  and wherein said Venezuelan Equine Encephalitis virus replicon particles elicit a protective immune response in a mammalian host.

15. The immunogenic composition of claim 14, wherein said protective immune response prevents infection of the lower respiratory tract by parainfluenza virus type 3 in a mammalian host.

16. The immunogenic composition of claim 14, wherein said protective immune response reduces the severity of infection of the upper respiratory tract by parainfluenza virus type 3 in a mammalian host.

17. The immunogenic composition of claim 14, further comprising a pharmaceutically acceptable carrier.

18. The immunogenic composition of claim 14, wherein said Venezuelan Equine Encephalitis virus replicase, said parainfluenza virus type 3 F glycoprotein, and said parainfluenza virus type 3 HN glycoprotein are encoded by the nucleic acid shown in SEQ ID NO: 1.

19. The immunogenic composition of claim 14, wherein said Venezuelan Equine Encephalitis virus replicase, said parainfluenza virus type 3 F glycoprotein, and said parainfluenza virus type 3 HN glycoprotein comprise the amino acid sequences set forth in SEQ ID NO:2; SEQ ID NO:3, and SEQ ID NO:4.

20. The immunogenic composition of claim 14, further comprising an adjuvant.

21. A method of immunizing a mammalian subject against infection of the respiratory tract by a parainfluenza virus, which method comprises administering to said subject an immunologically effective amount of:
  (a) an immunogenic composition comprising a population of Venezuelan Equine Encephalitis virus replicon particles (VRP) comprising Venezuelan Equine Encephalitis virus replicase proteins, Venezuelan Equine Encephalitis virus E glycoprotein, Venezuelan Equine Encephalitis virus E2 glycoprotein, and a Venezuelan Equine Encephalitis replicon vector with Venezuelan Equine Encephalitis virus replicase genes, parainfluenza virus F and HN glycoprotein genes; and
  (b) a pharmaceutical acceptable carrier,
  in an amount sufficient to elicit the immune response;
  wherein said population contains no detectable replication competent Venezuelan Equine Encephalitis virus;
  and wherein supernatants from cells infected with said replicon particles, when transferred to uninfected cell monolayers induce said cytopathic effects in the absence of said replicon particles.

22. The method of claim 21, wherein said parainfluenza virus is parainfluenza virus type 3.

23. The method of claim 22, wherein said HN glycoprotein is parainfluenza virus type 3 Hemagglutinin-Neuraminidase (HN) glycoprotein.

24. The method Of claim 22, wherein said F glycoprotein is parainfluenza virus type 3 Fusion (F) glycoprotein.

25. The method of claim 21, wherein said glycoprotein includes both parainfluenza virus type 3 F and HN glycoproteins.

26. The method of claim 21, wherein said infection is in the lower respiratory tract.

27. The method of claim 21, wherein said infection is in the upper respiratory tract.

28. A method of immunizing a mammalian subject against infection by parainfluenza virus type 3, which method comprises administering to said subject an immunologically effective amount of:
  (a) an immunogenic composition comprising a population of Venezuelan Equine Encephalitis virus replicon particles (VRP) comprising Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene; and
  (b) a pharmaceutically acceptable carrier,
  in an amount sufficient to elicit the immune response;
  wherein said population contains no detectable replication competent Venezuelan Equine Encephalitis virus;
  and wherein supernatants from cells infected with said replicon particles, when transferred to uninfected cell monolayers induce said cytopathic effects in the absence of said replicon particles.

29. The method of claim 28, wherein said infection is in the lower respiratory tract.

30. The method of claim 28, wherein said infection is in the upper respiratory tract.

31. The method of claim 28, wherein said immunogenic composition is administered two times.

32. The method of claim 28, wherein said immunogenic composition is administered three times.

33. An immunogenic composition comprising a population of self-propagating blebs comprising Venezuelan Equine Encephalitis virus replicase proteins, parainfluenzavirus type 3 F glycoprotein, parainfluenza virus type 3 HN glycoprotein and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene.

34. The immunogenic composition of claim 33, wherein said self-propagating blebs induce cytopathic effects when used to infect monolayers of BHK cultured cells.

35. The immunogenic composition of claim 34, wherein supernatants from cells infected with said self-propagating blebs, when transferred to uninfected cell monolayers induce said cytopathic effects in the absence of said replicon particles.

36. The immunogenic composition of claim 34, wherein said cytopathic effect' in BHK cultured cells is syncytia formation.

37. The immunogenic composition of claim 34, wherein said cytopathic effect in BHK cultured cells is monolayer disruption.

38. The immunogenic composition of claim 34, wherein said population contains no detectable replication competent Venezuelan Equine Encephalitis virus.

39. The immunogenic composition of claim 34, wherein said self-propagating blebs are obtained from the supernatant of cells infected with a population of Venezuelan Equine Encephalitis virus replicon particles (VRP), said replicon particles comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene.

40. An immunogenic composition comprising a population of self-propagating blebs comprising:
   Venezuelan Equine Encephalitis virus replicase proteins, parainfluenzavirus type 3 F glycoprotein, parainfluenza virus type 3 HN glycoprotein and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;
   wherein said self-propagating blebs are obtained from the supernatant of cells infected with a population of Venezuelan Equine Encephalitis virus replicon particles (VRP), said replicon particles comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;
   and wherein said population of self-propagating blebs contains no detectable replication competent Venezuelan Equine Encephalitis virus.

41. An immunogenic composition comprising a population of self-propagating blebs comprising Venezuelan Equine Encephalitis virus replicase proteins, parainfluenzavirus type 3 F glycoprotein, parainfluenza virus type 3 HN glycoprotein and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;
   wherein said self-propagating blebs are obtained from the supernatant of cells infected with a population of Venezuelan Equine Encephalitis virus replicon particles (VRP), said replicon particles comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;
   wherein said population of self-propagating blebs contains no detectable replication competent Venezuelan Equine Encephalitis virus;
   and wherein said population of self-propagating blebs induce cytopathic effect when used to infect monolayers of cultured BHK cells.

42. An immunogenic composition comprising a population of self-propagating blebs comprising Venezuelan Equine Encephalitis virus replicase proteins, parainfluenzavirus type 3 F glycoprotein, parainfluenza virus type 3 HN glycoprotein and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;
   wherein said self-propagating blebs are obtained from the supernatant of cells infected with a population of Venezuelan Equine Encephalitis virus replicon particles (VRP), said replicon particles comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;
   wherein said population of self-propagating blebs contains no detectable replication competent Venezuelan Equine Encephalitis virus;
   wherein said population of self-propagating blebs induce cytopathic effect when used to infect monolayers of cultured BHK cells;
   and wherein supernatants from cells infected with said population of self-propagating blebs, when transferred to uninfected cell monolayers induce said cytopathic effects in the absence of said replicon particles.

43. An immunogenic composition comprising a population of self-propagating blebs comprising:
   Venezuelan Equine Encephalitis virus replicase proteins, parainfluenzavirus type 3 F glycoprotein, parainfluenza virus type 3 HN glycoprotein and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;
   wherein said self-propagating blebs are obtained from the supernatant of cells infected with a population of Venezuelan Equine Encephalitis virus replicon particles (VRP), said replicon particles comprising Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;
   wherein said population of self-propagating blebs contains no detectable replication competent Venezuelan Equine Encephalitis virus;
   wherein said population of self-propagating blebs induce cytopathic effect when used to infect monolayers of cultured BHK cells;
   wherein supernatants from cells infected with said population of self-propagating blebs, when transferred to uninfected cell monolayers induce said cytopathic effects in the absence of said replicon particles;

and wherein said self-propagating blebs elicit a protective immune response in a mammalian host.

44. An immunogenic composition comprising a population of self-propagating blebs comprising Venezuelan Equine Encephalitis virus replicase proteins, parainfluenzavirus type 3 F glycoprotein, parainfluenza virus type 3 HN glycoprotein and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;

wherein said self-propagating blebs are obtained from the supernatant of cells infected with a population of Venezuelan Equine Encephalitis virus replicon particles (VRP), said replicon particles comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;

wherein said population of self-propagating blebs contains no detectable replication competent Venezuelan Equine Encephalitis virus;

wherein said population of self-propagating blebs induce cytopathic effect when used to infect monolayers of cultured BHK cells;

wherein supernatants from cells infected with said population of self-propagating blebs, when transferred to uninfected cell monolayers induce said cytopathic effects in the absence of said replicon particles;

and wherein said self-propagating blebs elicit a protective immune response in a mammalian host.

45. The immunogenic composition of claim 44, wherein said protective immune response prevents infection of the lower respiratory tract by parainfluenza virus type 3 in a mammalian host.

46. The immunogenic composition of claim 44, wherein said protective immune response reduces the severity of infection of the upper respiratory tract by parainfluenza virus type 3 in a mammalian host.

47. The immunogenic composition of claim 44, further comprising a pharmaceutically acceptable carrier.

48. The immunogenic composition of claim 44, further comprising an adjuvant.

49. An immunogenic composition comprising a population of self-propagating blebs comprising the Venezuelan Equine Encephalitis virus replicase proteins, parainfluenzavirus type 3 F glycoprotein, parainfluenza virus type 3 HN glycoprotein and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;

wherein said Venezuelan Equine Encephalitis virus replicase proteins, parainfluenza virus type 3 F glycoprotein, and parainfluenza virus type 3 HN glycoprotein have the amino acid sequences shown in SEQ ID NO: 2, SEQ ID NO: 3 and SEQ ID NO: 4, wherein said self-propagating blebs are obtained from the supernatant of cells infected with a population of Venezuelan Equine Encephalitis virus replicon particles (VRP), said replicon particles comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;

wherein said population of self-propagating blebs contains no detectable replication competent Venezuelan Equine Encephalitis virus;

wherein said population of self-propagating blebs induce cytopathic effect when used to infect monolayers of cultured BHK cells;

wherein supernatants from cells infected with said population of self-propagating blebs, when transferred to uninfected cell monolayers induce said cytopathic effects in the absence of said replicon particles;

and wherein said self-propagating blebs elicit a protective immune response in a mammalian host.

50. A method of immunizing a mammalian subject against infection of the respiratory tract by a parainfluenza virus, which method comprises administering to said subject an immunologically effective amount of:

(a) An immunogenic composition comprising a population of self-propagating blebs comprising Venezuelan Equine Encephalitis virus replicase proteins, parainfluenzavirus F glycoprotein, parainfluenza virus HN glycoprotein and a Venezuelan Equine Encephalitis replicon vector with Venezuelan Equine Encephalitis virus replicase genes, parainfluenza virus F glycoprotein gene, and parainfluenza virus HN glycoprotein gene;

(b) a pharmaceutical acceptable carrier, in an amount sufficient to elicit the immune response;

wherein said self-propagating blebs are obtained from the supernatant of cells infected with a population of Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus F glycoprotein gene, and parainfluenza virus HN glycoprotein gene;

wherein said population contains no detectable replication competent Venezuelan Equine Encephalitis virus;

and wherein supernatants from cells infected with said self-propagating blebs when transferred to uninfected cell monolayers induce cytopathic effects in the absence of said replicon particles.

51. The method of claim 50, wherein said parainfluenza virus is selected from the group consisting of parainfluenza virus type 1, parainfluenza virus type 2, parainfluenzavirus type 3, and parainfluenza virus type 4.

52. The method of claim 51, wherein said HN glycoprotein is parainfluenza virus type 3 Hemagglutinin-Neuraminidase (HN) glycoprotein.

53. The method of claim 51, wherein said F glycoprotein is parainfluenzavirus type 3 Fusion (F) glycoprotein.

54. The method of claim 50, wherein said glycoprotein includes both parainfluenza virus type 3 F glycoprotein and HN glycoproteins.

55. The method of claim 50, wherein said infection is in the lower respiratory tract.

56. The method of claim 50, wherein said infection is in the upper respiratory tract.

57. A method of immunizing a mammalian subject against infection by parainfluenza virus type 3, which method comprises administering to said subject an immunologically effective amount of:

(a) An immunogenic composition comprising a population of self-propagating blebs comprising Venezuelan Equine Encephalitis virus replicase proteins, parainfluenzavirus type 3 F glycoprotein, parainfluenza virus type 3 HN glycoprotein and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;

(b) a pharmaceutical acceptable carrier, in an amount sufficient to elicit the immune response;

wherein said self-propagating blebs are obtained from the supernatant of cells infected with a population of Venezuelan Equine Encephalitis virus replicon particles (VRP) said replicon particles comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;

wherein said population contains no detectable replication competent Venezuelan Equine Encephalitis virus;

and wherein supernatants from cells infected with said self-propagating blebs, when transferred to uninfected cell monolayers induce said cytopathic effects in the absence of said replicon particles.

58. The method of claim 57, wherein said infection is in the lower respiratory tract.

59. The method of claim 57, wherein said infection is in the upper respiratory tract.

60. The method of claim 57, wherein said immunogenic composition is administered two times.

61. The method of claim 57, wherein said immunogenic composition is administered three times.

62. A method of immunizing a mammalian subject against infection by parainfluenza virus type 3, which method comprises administering to said subject an immunologically effective amount of:

(a) An immunogenic composition comprising a population of self-propagating blebs comprising Venezuelan Equine Encephalitis virus replicase proteins, parainfluenzavirus type 3 F glycoprotein, parainfluenza virus type 3 HN glycoprotein and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene;

wherein said Venezuelan Equine Encephalitis virus replicase proteins, parainfluenza virus type 3 F glycoprotein, and parainfluenza virus type 3 HN glycoprotein have the amino acid sequences shown in SEQ ID NO: 2, SEQ ID NO: 3 and SEQ ID NO: 4;

(b) a pharmaceutical acceptable carrier, in an amount sufficient to elicit the immune response;

wherein said self-propagating blebs are obtained from the supernatant of cells infected with a population of Venezuelan Equine Encephalitis virus replicon particles (VRP), said replicon particles comprising the Venezuelan Equine Encephalitis virus replicase proteins, Venezuelan Equine Encephalitis virus E1 glycoprotein, Venezuelan Equine Encephalitis virus E2 glycoprotein, and a Venezuelan Equine Encephalitis replicon vector with Venezuelan Equine Encephalitis virus replicase genes, parainfluenza virus type 3 F glycoprotein gene, and parainfluenza virus type 3 HN glycoprotein gene:

wherein said population contains no-detectable replication competent Venezuelan Equine Encephalitis virus;

and wherein supernatants from cells infected with said self-propagating blebs, when transferred to uninfected cell monolayers induce said cytopathic effects in the absence of said replicon particles.

* * * * *

SEQUENCE LISTING

<160> NUMBER OF SEQ ID NOS: 4

<210> SEQ ID NO 1
<211> LENGTH: 13453
<212> TYPE: DNA
<213> ORGANISM: Artificial Sequence
<220> FEATURE:
<223> OTHER INFORMATION: This sequence is a chimeric sequence of
      Venezuelan equine encephalitis virus sequences and parainfluenza
      virus type 3 sequences.

<400> SEQUENCE: 1

```
ggtcgactct agaggatccc taatacgact cactatagat gggcggcgca tgagagaagc      60
ccagaccaat tacctaccca aaatggagaa agttcacgtt gacatcgagg aagacagccc     120
attcctcaga gctttgcagc ggagcttccc gcagtttgag gtagaagcca agcaggtcac     180
tgataatgac catgctaatg ccagagcgtt ttcgcatctg gcttcaaaac tgatcgaaac     240
ggaggtggac ccatccgaca cgatccttga cattggaagt gcgcccgccc gcagaatgta     300
ttctaagcac aagtatcatt gtatctgtcc gatgagatgt gcggaagatc cggacagatt     360
gtataagtat gcaactaagc tgaagaaaaa ctgtaaggaa ataactgata aggaattgga     420
caagaaaatg aaggagctcg ccgccgtcat gagcgaccct gacctggaaa ctgagactat     480
gtgcctccac gacgacgagt cgtgtcgcta cgaagggcaa gtcgctgttt accaggatgt     540
atacgcggtt gacggaccga caagtctcta tcaccaagcc aataagggag ttagagtcgc     600
ctactggata ggctttgaca ccaccccttt tatgtttaag aacttggctg gagcatatcc     660
atcatactct accaactggg ccgacgaaac cgtgttaacg gctcgtaaca taggcctatg     720
cagctctgac gttatggagc ggtcacgtag agggatgtcc attcttagaa agaagtattt     780
gaaaccatcc aacaatgttc tattctctgt tggctcgacc atctaccacg agaagaggga     840
cttactgagg agctggcacc tgccgtctgt atttcactta cgtggcaagc aaaattacac     900
atgtcggtgt gagactatag ttagttgcga cgggtacgtc gttaaaagaa tagctatcag     960
tccaggcctg tatgggaagc cttcaggcta tgctgctacg atgcaccgcg agggattctt    1020
gtgctgcaaa gtgacagaca cattgaacgg ggagagggtc tcttttcccg tgtgcacgta    1080
tgtgccagct acattgtgtg accaaatgac tggcatactg gcaacagatg tcagtgcgga    1140
cgacgcgcaa aaactgctgg ttgggctcaa ccagcgtata gtcgtcaacg gtcgcacccc    1200
gagaaacacc aataccatga aaaattacct ttttgcccgta gtggcccagg catttgctag    1260
gtgggcaaag gaatataagg aagatcaaga agatgaaagg ccactaggac tacgagatag    1320
acagttagtc atggggtgtt gttgggcttt tagaaggcac aagataacat ctatttataa    1380
gcgcccggat acccaaacca tcatcaaagt gaacagcgat ttccactcat tcgtgctgcc    1440
caggataggc agtaacacat tggagatcgg gctgagaaca agaatcagga aatgttaga    1500 ggagcacaag gagccgtcac ctctcattac cgccgaggac gtacaagaag ctaagtgcgc    1560
agccgatgag gctaaggagg tgcgtgaagc cgaggagttg cgcgcagctc taccaccttt    1620
ggcagctgat gttgaggagc ccactctgga agccgatgtc gacttgatgt tacaagaggc    1680
tggggccggc tcagtggaga cacctcgtgg cttgataaag gttaccagct acgctggcga    1740
ggacaagatc ggctcttacg ctgtgctttc tccgcaggct gtactcaaga gtgaaaaatt    1800
```

```
atcttgcatc caccctctcg ctgaacaagt catagtgata acacactctg gccgaaaagg    1860
gcgttatgcc gtggaaccat accatggtaa agtagtggtg ccagagggac atgcaatacc    1920
cgtccaggac tttcaagctc tgagtgaaag tgccaccatt gtgtacaacg aacgtgagtt    1980
cgtaaacagg tacctgcacc atattgccac acatggagga gcgctgaaca ctgatgaaga    2040
atattacaaa actgtcaagc ccagcgagca cgacggcgaa tacctgtacg acatcgacag    2100
gaaacagtgc gtcaagaaag aactagtcac tgggctaggg ctcacaggcg agctggtgga    2160
tcctcccttc catgaattcg cctacgagag tctgagaaca cgaccagccg ctccttacca    2220
agtaccaacc atagggggtgt atggcgtgcc aggatcaggc aagtctggca tcattaaaag    2280
cgcagtcacc aaaaaagatc tagtggtgag cgccaagaaa gaaaactgtg cagaaattat    2340
aagggacgtc aagaaaatga aagggctgga cgtcaatgcc agaactgtgg actcagtgct    2400
cttgaatgga tgcaaacacc ccgtagagac cctgtatatt gacgaagctt ttgcttgtca    2460
tgcaggtact ctcagagcgc tcatagccat tataagacct aaaaaggcag tgctctgcgg    2520
ggatcccaaa cagtgcggtt ttttttaacat gatgtgcctg aaagtgcatt ttaaccacga    2580
gatttgcaca caagtcttcc acaaaagcat ctctcgccgt tgcactaaat ctgtgacttc    2640
ggtcgtctca accttgtttt acgacaaaaa aatgagaacg acgaatccga aagagactaa    2700
gattgtgatt gacactaccg gcagtaccaa acctaagcag gacgatctca ttctcacttg    2760
tttcagaggg tgggtgaagc agttgcaaat agattacaaa ggcaacgaaa taatgacggc    2820
agctgcctct caagggctga cccgtaaagg tgtgtatgcc gttcggtaca aggtgaatga    2880
aaatcctctg tacgcaccca cctcagaaca tgtgaacgtc ctactgaccc gcacggagga    2940
ccgcatcgtg tggaaaacac tagccggcga cccatggata aaaacactga ctgccaagta    3000
ccctgggaat tcactgcca cgatagagga gtggcaagca gagcatgatg ccatcatgag    3060
gcacatcttg gagagaccgg accctaccga cgtcttccag aataaggcaa acgtgtgttg    3120
ggccaaggct ttagtgccgg tgctgaagac cgctggcata gacatgacca ctgaacaatg    3180
gaacactgtg gattattttg aaacggacaa agctcactca gcagagatag tattgaacca    3240
actatgcgtg aggttctttg gactcgatct ggactccggt ctattttctg cacccactgt    3300
tccgttatcc attaggaata atcactggga taactccccg tcgcctaaca tgtacgggct    3360
gaataaagaa gtggtccgtc agctctctcg caggtaccca caactgcctc gggcagttgc    3420
cactggaaga gtctatgaca tgaacactgg tacactgcgc aattatgatc cgcgcataaa    3480
cctagtacct gtaaacagaa gactgcctca tgctttagtc ctccaccata tgaacaccc    3540
acagagtgac ttttcttcat tcgtcagcaa attgaagggc agaactgtcc tggtggtcgg    3600
ggaaaagttg tccgtcccag gcaaaatggt tgactggttg tcagaccggc ctgaggctac    3660
cttcagagct cggctggatt taggcatccc aggtgatgtg cccaaatatg acataatatt    3720
tgttaatgtg aggaccccat ataaataccaa tcactatcag cagtgtgaag accatgccat    3780
taagcttagc atgttgacca agaaagcttg tctgcatctg aatcccggcg gaacctgtgt    3840
cagcataggt tatggttacg ctgacagggc cagcgaaagc atcattggtg ctatagcgcg    3900
gcagttcaag ttttcccggg tatgcaaacc gaaatcctca cttgaagaga cggaagttct    3960
gtttgtattc attgggtacg atcgcaaggc ccgtacgcac aatccttaca agctttcatc    4020
aaccttgacc aacatttata caggttccag actccacgaa gccggatgtg caccctcata    4080
tcatgtggtg cgagggggata ttgccacggc caccgaagga gtgattataa atgctgctaa    4140
```

```
cagcaaagga caacctggcg gaggggtgtg cggagcgctg tataagaaat tcccggaaag    4200
cttcgattta cagccgatcg aagtaggaaa agcgcgactg gtcaaaggtg cagctaaaca    4260
tatcattcat gccgtaggac caaacttcaa caaagtttcg gaggttgaag gtgacaaaca    4320
gttggcagag gcttatgagt ccatcgctaa gattgtcaac gataacaatt acaagtcagt    4380
agcgattcca ctgttgtcca ccggcatctt ttccgggaac aaagatcgac taacccaatc    4440
attgaaccat ttgctgacag cttttagacac cactgatgca gatgtagcca tatactgcag    4500
ggacaagaaa tgggaaatga ctctcaagga agcagtggct aggagagaag cagtggagga    4560
gatatgcata tccgacgact cttcagtgac agaacctgat gcagagctgg tgagggtgca    4620
tccgaagagt tctttggctg gaaggaaggg ctacagcaca agcgatggca aaactttctc    4680
atatttggaa gggaccaagt ttcaccaggc ggccaaggat atagcagaaa ttaatgccat    4740
gtggcccgtt gcaacggagg ccaatgagca ggtatgcatg tatatcctcg gagaaagcat    4800
gagcagtatt aggtcgaaat gccccgtcga agagtcggaa gcctccacac cacctagcac    4860
gctgccttgc ttgtgcatcc atgccatgac tccagaaaga gtacagcgcc taaaagcctc    4920
acgtccagaa caaattactg tgtgctcatc ctttccattg ccgaagtata gaatcactgg    4980
tgtgcagaag atccaatgct cccagcctat attgttctca ccgaaagtgc ctgcgtatat    5040
tcatccaagg aagtatctcg tggaaacacc accggtagac gagactccgg agccatcggc    5100
agagaaccaa tccacagagg ggacacctga acaaccacca cttataaccg aggatgagac    5160
caggactaga acgcctgagc cgatcatcat cgaagaggaa gaagaggata gcataagttt    5220
gctgtcagat ggcccgaccc accaggtgct gcaagtcgag gcagacattc acgggccgcc    5280
ctctgtatct agctcatcct ggtccattcc tcatgcatcc gactttgatg tggacagttt    5340
atccatactt gacaccctgg agggagctag cgtgaccagc ggggcaacgt cagccgagac    5400
taactcttac ttcgcaaaga gtatggagtt tctggcgcga ccggtgcctg cgcctcgaac    5460
agtattcagg aaccctccac atcccgctcc gcgcacaaga acaccgtcac ttgcacccag    5520
cagggcctgc tcgagaacca gcctagtttc caccccgcca ggcgtgaata gggtgatcac    5580
tagagaggag ctcgaggcgc ttaccccgtc acgcactcct agcaggtcgg tctcgagaac    5640
cagcctggtc tccaacccgc caggcgtaaa tagggtgatt acaagagagg agtttgaggc    5700
gttcgtagca caacaacaat gacggtttga tgcgggtgca tacatctttt cctccgacac    5760
cggtcaaggg catttacaac aaaaatcagt aaggcaaacg gtgctatccg aagtggtgtt    5820
ggagaggacc gaattggaga tttcgtatgc cccgcgcctc gaccaagaaa agaagaatt    5880
actacgcaag aaattacagt taaatcccac acctgctaac agaagcagat accagtccag    5940
gaaggtggag aacatgaaag ccataacagc tagacgtatt ctgcaaggcc tagggcatta    6000
tttgaaggca gaaggaaaag tggagtgcta ccgaacccctg catcctgttc ctttgtattc    6060
atctagtgtg aaccgtgcct tctcaagccc caaggtcgca gtggaagcct gtaacgccat    6120
gttgaaagag aactttccga ctgtggcttc ttactgtatt attccagagt acgatgccta    6180
tttggacatg gttgacggag cttcatgctg cttagacact gccagttttt gccctgcaaa    6240
gctgcgcagc tttccaaaga aacactccta tttggaaccc acaatacgat cggcagtgcc    6300
ttcagcgatc cagaacacgc tccagaacgt cctggcagct gccacaaaaa gaaattgcaa    6360
tgtcacgcaa atgagagaat tgcccgtatt ggattcggcg gcctttaatg tggaatgctt    6420
caagaaatat gcgtgtaata atgaatattg ggaaacgttt aaagaaaacc ccatcaggct    6480
tactgaagaa aacgtggtaa attacattac caaattaaaa ggaccaaaag ctgctgctct    6540
```

-continued

```
ttttgcgaag acacataatt tgaatatgtt gcaggacata ccaatggaca ggtttgtaat      6600
ggacttaaag agagacgtga aagtgactcc aggaacaaaa catactgaag aacggcccaa      6660
ggtacaggtg atccaggctg ccgatccgct agcaacagcg tatctgtgcg gaatccaccg      6720
agagctggtt aggagattaa atgcggtcct gcttccgaac attcatacac tgtttgatat      6780
gtcggctgaa gactttgacg ctattatagc cgagcacttc cagcctgggg attgtgttct      6840
ggaaactgac atcgcgtcgt ttgataaaag tgaggacgac gccatggctc tgaccgcgtt      6900
aatgattctg gaagacttag gtgtggacgc agagctgttg acgctgattg aggcggcttt      6960
cggcgaaatt tcatcaatac atttgcccac taaaactaaa tttaaattcg gagccatgat      7020
gaaatctgga atgttcctca cactgtttgt gaacacagtc attaacattg taatcgcaag      7080
cagagtgttg agagaacggc taaccggatc accatgtgca gcattcattg agatgacaa       7140 tatcgtgaaa ggagtcaaat cggacaaatt aatggcagac aggtgcgcca cctggttgaa      7200
tatggaagtc aagattatag atgctgtggt gggcgagaaa gcgccctatt tctgtggagg      7260
gtttattttg tgtgactccg tgaccggcac agcgtgccgt gtggcagacc ccctaaaaag      7320
gctgtttaag cttggcaaac ctctggcagc agacgatgaa catgatgatg acaggagaag      7380
ggcattgcat gaagagtcaa cacgctggaa ccgagtgggt attcttttcag agctgtgcaa      7440 ggcagtagaa tcaaggtatg aaaccgtagg aacttccatc atagttatgg ccatgactac      7500
tctagctagc agtgttaaat cattcagcta cctgagaggg gcccctataa ctctctacgg      7560
ctaacctgaa tggactacga catagtcgtt tgatccagcc gccaccatgc caacctcaat      7620
actgctaatt attacaacca tgattatggc atctttctgc caaatagata tcacaaaact      7680
acagcatgta ggtgtattgg ttaacagtcc caaagggatg aagatatcac aaaactttga      7740
aacaagatat ctaattttga gcctcatacc aaaaatagaa gattctaact cttgtggtga      7800
ccaacagatc aagcaataca agaggttatt ggatagactg atcattcctt tatatgatgg      7860
attaagatta cagaaggatg tgatagtgtc caatcaagaa tccatgaaaa cactgacccc      7920
cagaacaaaa cgattctttg gagggtaat tggaactatt gctctgggag tggcaacctc      7980
agcacaaatt acagcggcag ttgctctgtt gtgaagccaag caggcaagat cagacattga      8040
aaaactcaag gaagcaatca gggacacaaa caaagcagtg cagtcagtcc agagctccat      8100
aggaaatttg atagtagcaa ttaaatcggt ccaggattat gtcaacaaag aaatcgtgcc      8160
atcaattgcg agattaggtt gtgaagcagc aggacttcag ttaggaattg cattaacaca      8220
gcattactca gaattaacaa acatattcgg tgataacata ggatcgttac aagaaaaagg      8280
gataaaatta caaggtatag catcattata ccgcacaaat atcacagaga tattcacaac      8340
atcaacagtt gataaatatg atatttatga tctattattt acagaatcaa taaaggtgag      8400
agttatagat gttgacttga atgattactc aatcaccctc caagtcagac tccctttatt      8460
aactagactg ctgaacaccc agatttacag agtagattcc atatcatata acatccaaaa      8520
cagagaatgg tatatccctc ttcccagcca catcatgaca aaaggggcat ttctaggtgg      8580
agcagatgtc aaagaatgta tagaagcatt cagcagttat atatgcccctt ctgatccagg      8640 atttgtacta aaccatgaaa tggagagctg tttatcagga aacatatccc aatgtccaag      8700
aaccgtggtt aaatcagaca ttgttccaag atatgcattt gtcaatggag gagtggttgc      8760
aaattgtata acaaccacat gtacatgcaa cggtatcggt aatagaatca atcaaccacc      8820
tgatcaagga gtaaaaatta aacacataa agaatgtaat acaataggta tcaacggaat       8880
```

```
gctgttcaat acaaataaag aaggaactct tgcattttac acaccaaatg atataacatt    8940
aaacaattct gttgcacttg atccaattga catatcaatc gagctcaata aggccaaatc    9000
agatctagaa gagtcaaaag aatggataag aaggtcaaat caaaaactag attccattgg    9060
aaattggcat caatctagca ccacaatcat aattgttttg ataatgataa ttatattgtt    9120
tataattaat gtaacgataa ttataattgc agttaagtat tacagaattc aaaagagaaa    9180
tcgagtggat caaaatgata aaccatatgt attaacaaac aatgaaagc taaacttaat     9240
taaggcgcgc cccgcggtgt caaaaaccgc gtggacgtgg ttaacatccc tgctgggagg    9300
atcagccgta attattataa ttggcttggt gctggctact attgtggcca tgtacgtgct    9360
gaccaaccag aaacataatt gagaggggcc cctataactc tctacggcta acctgaatgg    9420
actacgacat cgataagctc ggaattcagc cgccaccatg gaatactgga agcacaccaa    9480
tcacgggaaa gatgctggta atgagctgga acatccatg gctactcatg gcaacaagat     9540
caccaacaag ataacatata tattatggac aataatcctg gtgttattat caatagtctt    9600
catcatagtg ctaattaatt ccatcaaaag tgaaaaagcc catgaatcat tgctacaaga    9660
cgtaaacaat gagtttatgg aagttacaga aaagatccaa atggcatcgg ataatattaa    9720
tgatctaata cagtcaggag tgaatacaag gcttcttaca attcagagtc atgtccagaa    9780
ttatataccg atatcattga cacaacaaat gtcggatctt aggaaattca ttagtgaaat    9840
tacaattagg aatgataatc aagaagtgcc tccacaaaga ataacacatg atgtgggcat    9900
aaaacccttta aatccagatg attttttggag atgcacgtct ggtcttccat ctttaatgaa    9960
aactccaaaa ataaggttaa tgccggggcc gggattatta gctatgccaa cgactgttga    10020
tggctgtgtt agaactccgt ccttagttat aaatgatctg atttatgctt atacctcgaa    10080
tctaattact cgaggttgcc aggatatagg aaaatcatat caagtattac agataggat    10140
aataactgta aactcagact tggtacctga cttaaatcct aggatctctc atactttcaa    10200
cataaatgac aatagaaagt catgttctct agcactccta aacacagatg tatatcaact    10260
gtgttcgact cccaaagttg atgaaagatc agattatgca tcatcaggca tagaagatat    10320
tgtacttgat atcgtcaatc atgatggttc aatctcaaca acaagattta agaacaataa    10380
tataagtttt gatcaaccat atgcggcatt atacccatct gttggaccag ggatatacta    10440
caaaggcaaa ataatatttc tcgggtatgg aggtcttgaa catccaataa atgagaatgc    10500
aatctgcaac acaactgggt gtcccgggaa aacgcagaga gactgcaatc aggcatctca    10560
tagtccttgg ttttcagaca gaaggatggt caactccatt attgttgttg acaagggctt    10620
aaactcaatt ccaaaactga aggtatggac gatatccatg agacaaaatt actggggtc     10680
agaaggaagg ctacttctac taggtaacaa gatctatata tatacaagat ctacaagttg    10740
gcatagcaag ttacaattag gaataattga tattactgat tacagtgata taagaataaa    10800
atggacatgg cataatgtgc tatcaagacc aggaaacaat gaatgtccat ggggacattc    10860
atgcccagat ggatgtataa caggagtata tactgatgca tatccactca atcccacagg    10920
gagcattgtg tcatctgtca tattagactc gcaaaaatcg agagtaaacc cagtcataac    10980
ttactcaaca tcaactgaaa gggtaaacga gctggccatc cgaaacaaaa cactctcagc    11040
tggatataca acaacgagct gcattacaca ctataacaaa ggatattgtt ttcatatagt    11100
agaaataaat cataaaagct tagacacatt ccaacctatg ttgttcaaaa cagagattcc    11160
aaaaagctgc agttaaggat cctctagagt cgacctgcag ccaagcttat cgatacagca    11220
gcaattggca agctgcttac atagaactcg cggcgattgg catgccgctt taaaattttt    11280
```

```
attttatttt tcttttcttt tccgaatcgg attttgtttt taatatttca aaaaaaaaaa    11340
aaaaaaaaaa gggcggccgc cgagctcgaa ttcgtaatca tgtcatagct gtttcctgtg    11400
tgaaattgtt atccgctcac aattccacac aacatacgag ccggaagcat aaagtgtaaa    11460
gcctggggtg cctaatgagt gagctaactc acattaattg cgttgcgctc actgcccgct    11520
ttccagtcgg gaaacctgtc gtgccagtcg aggggaatta ttcttgaag acgaaagggc     11580 caggtggcac ttttcgggga aatgtgcgcg gaaccctat ttgtttattt ttctaaatac      11640
attcaaatat gtatccgctc atgagacaat aaccctgata aatgcttcaa taatattgaa    11700
aaaggaagag tatgagtatt caacatttcc gtgtcgccct tattccctt tttgcggcat     11760 tttgccttcc tgtttttgct cacccagaaa cgctggtgaa agtaaaagat gctgaagatc    11820
agttgggtgc acgcgtgggt tacatcgaac tggatctcaa cagcggtaag atccttgaga   11880
gttttcgccc cgaagaacgt tttccaatga tgagcacttt taaagttctg ctatgtggcg   11940
cggtattatc ccgtgttgac gccgggcaag agcaactcgg tcgccgcata cactattctc    12000
agaatgactt ggttgagtac tcaccagtca cagaaaagca tcttacggat ggcatgacag   12060
taagagaatt atgcagtgct gccataacca tgagtgataa cactgcggcc aacttacttc   12120
tgacaacgat cggaggaccg aaggagctaa ccgcttttt tgcacaacatg ggggatcatg    12180 taactcgcct tgatcgttgg gaaccggagc tgaatgaagc cataccaaac gacgagcgtg   12240
acaccacgat gcctgtagca atggcaacaa cgttgcgcaa actattaact ggcgaactac    12300
ttactctagc ttcccggcaa caattaatag actggatgga ggcggataaa gttgcaggac    12360
cacttctgcg ctcggccctt ccggctggct ggtttattgc tgataaatct ggagccggtg   12420
agcgtgggtc tcgcggtatc attgcagcac tggggccaga tggtaagccc tcccgtatcg   12480
tagttatcta cacgacgggg agtcaggcaa ctatggatga acgaaataga cagatcgctg    12540
agataggtgc ctcactgatt aagcattggt aactgtcaga ccaagtttac tcatatatac    12600
tttagattga tttaaaactt cattttttaat ttaaaaggat ctaggtgaag atccttttg    12660 ataatctcat gaccaaaatc ccttaacgtg agttttcgtt ccactgagcg tcagaccccg   12720
tagaaaagat caaaggatct tcttgagatc ctttttttct gcgcgtaatc tgctgcttgc    12780
aaacaaaaaa accaccgcta ccagcggtgg tttgtttgcc ggatcaagag ctaccaactc    12840 ttttccgaa ggtaactggc ttcagcagag cgcagatacc aaatactgtc cttctagtgt     12900
agccgtagtt aggccaccac ttcaagaact ctgtagcacc gcctacatac ctcgctctgc    12960
taatcctgtt accagtggct gctgccagtg gcgataagtc gtgtcttacc gggttggact    13020
caagacgata gttaccggat aaggcgcagc ggtcgggctg aacggggggt tcgtgcacac   13080
agcccagctt ggagcgaacg acctacaccg aactgagata cctacagcgt gagctatgag   13140
aaagcgccac gcttcccgaa gggagaaagg cggacaggta tccggtaagc ggcagggtcg   13200
gaacaggaga gcgcacgagg gagcttccag ggggaaacgc ctggtatctt tatagtcctg    13260
tcgggtttcg ccacctctga cttgagcgtc gatttttgtg atgctcgtca gggggggcgga   13320 gcctatggaa aaacgccagc aacgcgctgg cgaaggggg atgtgctgca aggcgattaa    13380
gttgggtaac gccagggttt tcccagtcac gacgttgtaa aacgacggcc agtgccaagc   13440
ttgcatgcct gca                                                      13453
```

<210> SEQ ID NO 2
<211> LENGTH: 2492
<212> TYPE: PRT

<213> ORGANISM: Venezuelan equine encephalitis virus non-structural proteins 1-4

<400> SEQUENCE: 2

```
Met Glu Lys Val His Val Asp Ile Glu Glu Ser Pro Phe Leu Arg
1               5                   10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser
                35                  40                  45

Lys Leu Ile Glu Thr Glu Val Asp Pro Ser Asp Thr Ile Leu Asp Ile
50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190

Pro Ser Tyr Ser Thr Asn Trp Ala Asp Glu Thr Val Leu Thr Ala Arg
        195                 200                 205

Asn Ile Gly Leu Cys Ser Ser Asp Val Met Glu Arg Ser Arg Arg Gly
210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
370                 375                 380

Pro Val Val Ala Gln Ala Phe Ala Arg Trp Ala Lys Glu Tyr Lys Glu
385                 390                 395                 400
```

-continued

```
Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
    450                 455                 460

Arg Thr Arg Ile Arg Lys Met Leu Glu Glu His Lys Glu Pro Ser Pro
465                 470                 475                 480

Leu Ile Thr Ala Glu Asp Val Gln Glu Ala Lys Cys Ala Ala Asp Glu
                485                 490                 495

Ala Lys Glu Val Arg Glu Ala Glu Leu Arg Ala Ala Leu Pro Pro
            500                 505                 510

Leu Ala Ala Asp Val Glu Glu Pro Thr Leu Glu Ala Asp Val Asp Leu
        515                 520                 525

Met Leu Gln Glu Ala Gly Ala Gly Ser Val Glu Thr Pro Arg Gly Leu
    530                 535                 540

Ile Lys Val Thr Ser Tyr Ala Gly Glu Asp Lys Ile Gly Ser Tyr Ala
545                 550                 555                 560

Val Leu Ser Pro Gln Ala Val Leu Lys Ser Lys Leu Ser Cys Ile
                565                 570                 575

His Pro Leu Ala Glu Gln Val Ile Val Ile Thr His Ser Gly Arg Lys
        580                 585                 590

Gly Arg Tyr Ala Val Glu Pro Tyr His Gly Lys Val Val Pro Glu
    595                 600                 605

Gly His Ala Ile Pro Val Gln Asp Phe Gln Ala Leu Ser Glu Ser Ala
    610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
            645                 650                 655

Thr Val Lys Pro Ser Glu His Asp Gly Glu Tyr Leu Tyr Asp Ile Asp
        660                 665                 670

Arg Lys Gln Cys Val Lys Lys Glu Leu Val Thr Gly Leu Gly Leu Thr
    675                 680                 685

Gly Glu Leu Val Asp Pro Pro Phe His Glu Phe Ala Tyr Glu Ser Leu
    690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
                725                 730                 735

Lys Lys Asp Leu Val Val Ser Ala Lys Lys Glu Asn Cys Ala Glu Ile
            740                 745                 750

Ile Arg Asp Val Lys Lys Met Lys Gly Leu Asp Val Asn Ala Arg Thr
        755                 760                 765

Val Asp Ser Val Leu Leu Asn Gly Cys Lys His Pro Val Glu Thr Leu
    770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
                805                 810                 815
```

-continued

```
Gln Cys Gly Phe Phe Asn Met Met Cys Leu Lys Val His Phe Asn His
                820             825                 830

Glu Ile Cys Thr Gln Val Phe His Lys Ser Ile Ser Arg Arg Cys Thr
                835             840                 845

Lys Ser Val Thr Ser Val Val Ser Thr Leu Phe Tyr Asp Lys Lys Met
850             855                 860

Arg Thr Thr Asn Pro Lys Glu Thr Lys Ile Val Ile Asp Thr Thr Gly
865             870                 875                 880

Ser Thr Lys Pro Lys Gln Asp Asp Leu Ile Leu Thr Cys Phe Arg Gly
                885             890                 895

Trp Val Lys Gln Leu Gln Ile Asp Tyr Lys Gly Asn Glu Ile Met Thr
                900             905                 910

Ala Ala Ala Ser Gln Gly Leu Thr Arg Lys Gly Val Tyr Ala Val Arg
                915             920                 925

Tyr Lys Val Asn Glu Asn Pro Leu Tyr Ala Pro Thr Ser Glu His Val
930             935                 940

Asn Val Leu Leu Thr Arg Thr Glu Asp Arg Ile Val Trp Lys Thr Leu
945             950                 955                 960

Ala Gly Asp Pro Trp Ile Lys Thr Leu Thr Ala Lys Tyr Pro Gly Asn
                965             970                 975

Phe Thr Ala Thr Ile Glu Glu Trp Gln Ala Glu His Asp Ala Ile Met
                980             985                 990

Arg His Ile Leu Glu Arg Pro Asp  Pro Thr Asp Val Phe  Gln Asn Lys
                995              1000                1005

Ala Asn  Val Cys Trp Ala Lys  Ala Leu Val Pro Val  Leu Lys Thr
     1010                 1015                 1020

Ala Gly  Ile Asp Met Thr Thr  Glu Gln Trp Asn Thr  Val Asp Tyr
     1025                 1030                 1035

Phe Glu  Thr Asp Lys Ala His  Ser Ala Glu Ile Val  Leu Asn Gln
     1040                 1045                 1050

Leu Cys  Val Arg Phe Phe Gly  Leu Asp Leu Asp Ser  Gly Leu Phe
     1055                 1060                 1065

Ser Ala  Pro Thr Val Pro Leu  Ser Ile Arg Asn Asn  His Trp Asp
     1070                 1075                 1080

Asn Ser  Pro Ser Pro Asn Met  Tyr Gly Leu Asn Lys  Glu Val Val
     1085                 1090                 1095

Arg Gln  Leu Ser Arg Arg Tyr  Pro Gln Leu Pro Arg  Ala Val Ala
     1100                 1105                 1110

Thr Gly  Arg Val Tyr Asp Met  Asn Thr Gly Thr Leu  Arg Asn Tyr
     1115                 1120                 1125

Asp Pro  Arg Ile Asn Leu Val  Pro Val Asn Arg Arg  Leu Pro His
     1130                 1135                 1140

Ala Leu  Val Leu His His Asn  Glu His Pro Gln Ser  Asp Phe Ser
     1145                 1150                 1155

Ser Phe  Val Ser Lys Leu Lys  Gly Arg Thr Val Leu  Val Val Gly
     1160                 1165                 1170

Glu Lys  Leu Ser Val Pro Gly  Lys Met Val Asp Trp  Leu Ser Asp
     1175                 1180                 1185

Arg Pro  Glu Ala Thr Phe Arg  Ala Arg Leu Asp Leu  Gly Ile Pro
     1190                 1195                 1200

Gly Asp  Val Pro Lys Tyr Asp  Ile Ile Phe Val Asn  Val Arg Thr
     1205                 1210                 1215

Pro Tyr  Lys Tyr His His Tyr  Gln Gln Cys Glu Asp  His Ala Ile
```

-continued

```
            1220                1225                1230
Lys Leu Ser Met Leu Thr Lys Lys Ala Cys Leu His Leu Asn Pro
        1235                1240                1245
Gly Gly Thr Cys Val Ser Ile Gly Tyr Gly Tyr Ala Asp Arg Ala
        1250                1255                1260
Ser Glu Ser Ile Ile Gly Ala Ile Ala Arg Gln Phe Lys Phe Ser
        1265                1270                1275
Arg Val Cys Lys Pro Lys Ser Ser Leu Glu Glu Thr Glu Val Leu
        1280                1285                1290
Phe Val Phe Ile Gly Tyr Asp Arg Lys Ala Arg Thr His Asn Pro
        1295                1300                1305
Tyr Lys Leu Ser Ser Thr Leu Thr Asn Ile Tyr Thr Gly Ser Arg
        1310                1315                1320
Leu His Glu Ala Gly Cys Ala Pro Ser Tyr His Val Val Arg Gly
        1325                1330                1335
Asp Ile Ala Thr Ala Thr Glu Gly Val Ile Ile Asn Ala Ala Asn
        1340                1345                1350
Ser Lys Gly Gln Pro Gly Gly Gly Val Cys Gly Ala Leu Tyr Lys
        1355                1360                1365
Lys Phe Pro Glu Ser Phe Asp Leu Gln Pro Ile Glu Val Gly Lys
        1370                1375                1380
Ala Arg Leu Val Lys Gly Ala Ala Lys His Ile His Ile His Ala Val
        1385                1390                1395
Gly Pro Asn Phe Asn Lys Val Ser Glu Val Glu Gly Asp Lys Gln
        1400                1405                1410
Leu Ala Glu Ala Tyr Glu Ser Ile Ala Lys Ile Val Asn Asp Asn
        1415                1420                1425
Asn Tyr Lys Ser Val Ala Ile Pro Leu Leu Ser Thr Gly Ile Phe
        1430                1435                1440
Ser Gly Asn Lys Asp Arg Leu Thr Gln Ser Leu Asn His Leu Leu
        1445                1450                1455
Thr Ala Leu Asp Thr Thr Asp Ala Asp Val Ala Ile Tyr Cys Arg
        1460                1465                1470
Asp Lys Lys Trp Glu Met Thr Leu Lys Glu Ala Val Ala Arg Arg
        1475                1480                1485
Glu Ala Val Glu Glu Ile Cys Ile Ser Asp Asp Ser Ser Val Thr
        1490                1495                1500
Glu Pro Asp Ala Glu Leu Val Arg Val His Pro Lys Ser Ser Leu
        1505                1510                1515
Ala Gly Arg Lys Gly Tyr Ser Thr Ser Asp Gly Lys Thr Phe Ser
        1520                1525                1530
Tyr Leu Glu Gly Thr Lys Phe His Gln Ala Ala Lys Asp Ile Ala
        1535                1540                1545
Glu Ile Asn Ala Met Trp Pro Val Ala Thr Glu Ala Asn Glu Gln
        1550                1555                1560
Val Cys Met Tyr Ile Leu Gly Glu Ser Met Ser Ser Ile Arg Ser
        1565                1570                1575
Lys Cys Pro Val Glu Glu Ser Glu Ala Ser Thr Pro Pro Ser Thr
        1580                1585                1590
Leu Pro Cys Leu Cys Ile His Ala Met Thr Pro Glu Arg Val Gln
        1595                1600                1605
Arg Leu Lys Ala Ser Arg Pro Glu Gln Ile Thr Val Cys Ser Ser
        1610                1615                1620
```

```
Phe Pro Leu Pro Lys Tyr Arg Ile Thr Gly Val Gln Lys Ile Gln
    1625            1630            1635

Cys Ser Gln Pro Ile Leu Phe Ser Pro Lys Val Pro Ala Tyr Ile
    1640            1645            1650

His Pro Arg Lys Tyr Leu Val Glu Thr Pro Pro Val Asp Glu Thr
    1655            1660            1665

Pro Glu Pro Ser Ala Glu Asn Gln Ser Thr Glu Gly Thr Pro Glu
    1670            1675            1680

Gln Pro Pro Leu Ile Thr Glu Asp Glu Thr Arg Thr Arg Thr Pro
    1685            1690            1695

Glu Pro Ile Ile Ile Glu Glu Glu Glu Asp Ser Ile Ser Leu
    1700            1705            1710

Leu Ser Asp Gly Pro Thr His Gln Val Leu Gln Val Glu Ala Asp
    1715            1720            1725

Ile His Gly Pro Pro Ser Val Ser Ser Ser Ser Trp Ser Ile Pro
    1730            1735            1740

His Ala Ser Asp Phe Asp Val Asp Ser Leu Ser Ile Leu Asp Thr
    1745            1750            1755

Leu Glu Gly Ala Ser Val Thr Ser Gly Ala Thr Ser Ala Glu Thr
    1760            1765            1770

Asn Ser Tyr Phe Ala Lys Ser Met Glu Phe Leu Ala Arg Pro Val
    1775            1780            1785

Pro Ala Pro Arg Thr Val Phe Arg Asn Pro Pro His Pro Ala Pro
    1790            1795            1800

Arg Thr Arg Thr Pro Ser Leu Ala Pro Ser Arg Ala Cys Ser Arg
    1805            1810            1815

Thr Ser Leu Val Ser Thr Pro Pro Gly Val Asn Arg Val Ile Thr
    1820            1825            1830

Arg Glu Glu Leu Glu Ala Leu Thr Pro Ser Arg Thr Pro Ser Arg
    1835            1840            1845

Ser Val Ser Arg Thr Ser Leu Val Ser Asn Pro Pro Gly Val Asn
    1850            1855            1860

Arg Val Ile Thr Arg Glu Glu Phe Glu Ala Phe Val Ala Gln Gln
    1865            1870            1875

Gln Arg Phe Asp Ala Gly Ala Tyr Ile Phe Ser Ser Asp Thr Gly
    1880            1885            1890

Gln Gly His Leu Gln Gln Lys Ser Val Arg Gln Thr Val Leu Ser
    1895            1900            1905

Glu Val Val Leu Glu Arg Thr Glu Leu Glu Ile Ser Tyr Ala Pro
    1910            1915            1920

Arg Leu Asp Gln Glu Lys Glu Glu Leu Leu Arg Lys Lys Leu Gln
    1925            1930            1935

Leu Asn Pro Thr Pro Ala Asn Arg Ser Arg Tyr Gln Ser Arg Lys
    1940            1945            1950

Val Glu Asn Met Lys Ala Ile Thr Ala Arg Arg Ile Leu Gln Gly
    1955            1960            1965

Leu Gly His Tyr Leu Lys Ala Glu Gly Lys Val Glu Cys Tyr Arg
    1970            1975            1980

Thr Leu His Pro Val Pro Leu Tyr Ser Ser Ser Val Asn Arg Ala
    1985            1990            1995

Phe Ser Ser Pro Lys Val Ala Val Glu Ala Cys Asn Ala Met Leu
    2000            2005            2010
```

```
Lys Glu Asn Phe Pro Thr Val Ala Ser Tyr Cys Ile Ile Pro Glu
2015                2020                2025

Tyr Asp Ala Tyr Leu Asp Met Val Asp Gly Ala Ser Cys Cys Leu
2030                2035                2040

Asp Thr Ala Ser Phe Cys Pro Ala Lys Leu Arg Ser Phe Pro Lys
2045                2050                2055

Lys His Ser Tyr Leu Glu Pro Thr Ile Arg Ser Ala Val Pro Ser
2060                2065                2070

Ala Ile Gln Asn Thr Leu Gln Asn Val Leu Ala Ala Ala Thr Lys
2075                2080                2085

Arg Asn Cys Asn Val Thr Gln Met Arg Glu Leu Pro Val Leu Asp
2090                2095                2100

Ser Ala Ala Phe Asn Val Glu Cys Phe Lys Lys Tyr Ala Cys Asn
2105                2110                2115

Asn Glu Tyr Trp Glu Thr Phe Lys Glu Asn Pro Ile Arg Leu Thr
2120                2125                2130

Glu Glu Asn Val Val Asn Tyr Ile Thr Lys Leu Lys Gly Pro Lys
2135                2140                2145

Ala Ala Ala Leu Phe Ala Lys Thr His Asn Leu Asn Met Leu Gln
2150                2155                2160

Asp Ile Pro Met Asp Arg Phe Val Met Asp Leu Lys Arg Asp Val
2165                2170                2175

Lys Val Thr Pro Gly Thr Lys His Thr Glu Glu Arg Pro Lys Val
2180                2185                2190

Gln Val Ile Gln Ala Ala Asp Pro Leu Ala Thr Ala Tyr Leu Cys
2195                2200                2205

Gly Ile His Arg Glu Leu Val Arg Arg Leu Asn Ala Val Leu Leu
2210                2215                2220

Pro Asn Ile His Thr Leu Phe Asp Met Ser Ala Glu Asp Phe Asp
2225                2230                2235

Ala Ile Ile Ala Glu His Phe Gln Pro Gly Asp Cys Val Leu Glu
2240                2245                2250

Thr Asp Ile Ala Ser Phe Asp Lys Ser Glu Asp Asp Ala Met Ala
2255                2260                2265

Leu Thr Ala Leu Met Ile Leu Glu Asp Leu Gly Val Asp Ala Glu
2270                2275                2280

Leu Leu Thr Leu Ile Glu Ala Ala Phe Gly Glu Ile Ser Ser Ile
2285                2290                2295

His Leu Pro Thr Lys Thr Lys Phe Lys Phe Gly Ala Met Met Lys
2300                2305                2310

Ser Gly Met Phe Leu Thr Leu Phe Val Asn Thr Val Ile Asn Ile
2315                2320                2325

Val Ile Ala Ser Arg Val Leu Arg Glu Arg Leu Thr Gly Ser Pro
2330                2335                2340

Cys Ala Ala Phe Ile Gly Asp Asp Asn Ile Val Lys Gly Val Lys
2345                2350                2355

Ser Asp Lys Leu Met Ala Asp Arg Cys Ala Thr Trp Leu Asn Met
2360                2365                2370

Glu Val Lys Ile Ile Asp Ala Val Val Gly Glu Lys Ala Pro Tyr
2375                2380                2385

Phe Cys Gly Gly Phe Ile Leu Cys Asp Ser Val Thr Gly Thr Ala
2390                2395                2400

Cys Arg Val Ala Asp Pro Leu Lys Arg Leu Phe Lys Leu Gly Lys
```

```
                       2405                2410                2415

Pro Leu Ala Ala Asp Asp Glu His Asp Asp Arg Arg Arg Ala
    2420                2425                2430

Leu His Glu Glu Ser Thr Arg Trp Asn Arg Val Gly Ile Leu Ser
    2435                2440                2445

Glu Leu Cys Lys Ala Val Glu Ser Arg Tyr Glu Thr Val Gly Thr
    2450                2455                2460

Ser Ile Ile Val Met Ala Met Thr Thr Leu Ala Ser Ser Val Lys
    2465                2470                2475

Ser Phe Ser Tyr Leu Arg Gly Ala Pro Ile Thr Leu Tyr Gly
    2480                2485                2490

<210> SEQ ID NO 3
<211> LENGTH: 539
<212> TYPE: PRT
<213> ORGANISM: parainfluenza virus type 3 Fusion (F) protein sequence

<400> SEQUENCE: 3

Met Pro Thr Ser Ile Leu Leu Ile Ile Thr Thr Met Ile Met Ala Ser
1               5                   10                  15

Phe Cys Gln Ile Asp Ile Thr Lys Leu Gln His Val Gly Val Leu Val
                20                  25                  30

Asn Ser Pro Lys Gly Met Lys Ile Ser Gln Asn Phe Glu Thr Arg Tyr
            35                  40                  45

Leu Ile Leu Ser Leu Ile Pro Lys Ile Glu Asp Ser Asn Ser Cys Gly
        50                  55                  60

Asp Gln Gln Ile Lys Gln Tyr Lys Arg Leu Leu Asp Arg Leu Ile Ile
65                  70                  75                  80

Pro Leu Tyr Asp Gly Leu Arg Leu Gln Lys Asp Val Ile Val Ser Asn
                85                  90                  95

Gln Glu Ser Asn Glu Asn Thr Asp Pro Arg Thr Lys Arg Phe Phe Gly
            100                 105                 110

Gly Val Ile Gly Thr Ile Ala Leu Gly Val Ala Thr Ser Ala Gln Ile
        115                 120                 125

Thr Ala Ala Val Ala Leu Val Glu Ala Lys Gln Ala Arg Ser Asp Ile
130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Lys Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Ser Leu Gln Glu Lys
    210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
            260                 265                 270

Asp Tyr Ser Ile Thr Leu Gln Val Arg Leu Pro Leu Leu Thr Arg Leu
        275                 280                 285
```

-continued

Leu Asn Thr Gln Ile Tyr Arg Val Asp Ser Ile Ser Tyr Asn Ile Gln
    290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Met
            340                 345                 350

Glu Ser Cys Leu Ser Gly Asn Ile Ser Gln Cys Pro Arg Thr Val Val
        355                 360                 365

Lys Ser Asp Ile Val Pro Arg Tyr Ala Phe Val Asn Gly Gly Val Val
370                 375                 380

Ala Asn Cys Ile Thr Thr Thr Cys Thr Cys Asn Gly Ile Gly Asn Arg
385                 390                 395                 400

Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
            420                 425                 430

Gly Thr Leu Ala Phe Tyr Thr Pro Asn Asp Ile Thr Leu Asn Asn Ser
        435                 440                 445

Val Ala Leu Asp Pro Ile Asp Ile Ser Ile Glu Leu Asn Lys Ala Lys
450                 455                 460

Ser Asp Leu Glu Glu Ser Lys Glu Trp Ile Arg Arg Ser Asn Gln Lys
465                 470                 475                 480

Leu Asp Ser Ile Gly Asn Trp His Gln Ser Ser Thr Thr Ile Ile Ile
                485                 490                 495

Val Leu Ile Met Ile Ile Leu Phe Ile Ile Asn Val Thr Ile Ile
            500                 505                 510

Ile Ile Ala Val Lys Tyr Tyr Arg Ile Gln Lys Arg Asn Arg Val Asp
        515                 520                 525

Gln Asn Asp Lys Pro Tyr Val Leu Thr Asn Lys
530                 535

<210> SEQ ID NO 4
<211> LENGTH: 572
<212> TYPE: PRT
<213> ORGANISM: parainfluenza virus type 3 HN protein sequence

<400> SEQUENCE: 4

Met Glu Tyr Trp Lys His Thr Asn His Gly Lys Asp Ala Gly Asn Glu
1               5                   10                  15

Leu Glu Thr Ser Met Ala Thr His Gly Asn Lys Ile Thr Asn Lys Ile
            20                  25                  30

Thr Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
    50                  55                  60

Leu Leu Gln Asp Val Asn Asn Glu Phe Met Glu Val Thr Glu Lys Ile
65                  70                  75                  80

Gln Met Ala Ser Asp Asn Ile Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110

Ser Leu Thr Gln Gln Met Ser Asp Leu Arg Lys Phe Ile Ser Glu Ile
        115                 120                 125

```
Thr Ile Arg Asn Asp Asn Gln Glu Val Pro Pro Gln Arg Ile Thr His
        130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Val Arg
            180                 185                 190

Thr Pro Ser Leu Val Ile Asn Asp Leu Ile Tyr Ala Tyr Thr Ser Asn
        195                 200                 205

Leu Ile Thr Arg Gly Cys Gln Asp Ile Gly Lys Ser Tyr Gln Val Leu
    210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Thr Asp Val Tyr Gln Leu Cys Ser Thr Pro
            260                 265                 270

Lys Val Asp Glu Arg Ser Asp Tyr Ala Ser Ser Gly Ile Glu Asp Ile
        275                 280                 285

Val Leu Asp Ile Val Asn His Asp Gly Ser Ile Ser Thr Thr Arg Phe
    290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335

Tyr Gly Gly Leu Glu His Pro Ile Asn Glu Asn Ala Ile Cys Asn Thr
            340                 345                 350

Thr Gly Cys Pro Gly Lys Thr Gln Arg Asp Cys Asn Gln Ala Ser His
        355                 360                 365

Ser Pro Trp Phe Ser Asp Arg Arg Met Val Asn Ser Ile Ile Val Val
    370                 375                 380

Asp Lys Gly Leu Asn Ser Ile Pro Lys Leu Lys Val Trp Thr Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
            420                 425                 430

Gln Leu Gly Ile Ile Asp Ile Thr Asp Tyr Ser Asp Ile Arg Ile Lys
        435                 440                 445

Trp Thr Trp His Asn Val Leu Ser Arg Pro Gly Asn Asn Glu Cys Pro
    450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ser
            500                 505                 510

Thr Glu Arg Val Asn Glu Leu Ala Ile Arg Asn Lys Thr Leu Ser Ala
        515                 520                 525

Gly Tyr Thr Thr Thr Ser Cys Ile Thr His Tyr Asn Lys Gly Tyr Cys
    530                 535                 540
```

```
-continued

Phe His Ile Val Glu Ile Asn His Lys Ser Leu Asp Thr Phe Gln Pro
545                 550                 555                 560

Met Leu Phe Lys Thr Glu Ile Pro Lys Ser Cys Ser
                565                 570
```